United States Patent
Hepworth et al.

(10) Patent No.: US 11,951,248 B2
(45) Date of Patent: Apr. 9, 2024

(54) AEROSOL PROVISION SYSTEMS

(71) Applicant: Nicoventures Trading Limited, London (GB)

(72) Inventors: Richard Hepworth, London (GB); Patrick Moloney, London (GB); Walid Abi Aoun, London (GB)

(73) Assignee: NICOVENTURES TRADING LIMITED, London (GB)

( * ) Notice: Subject to any disclaimer, the term of this patent is extended or adjusted under 35 U.S.C. 154(b) by 456 days.

(21) Appl. No.: 16/754,503

(22) PCT Filed: Oct. 11, 2018

(86) PCT No.: PCT/GB2018/052912
§ 371 (c)(1),
(2) Date: Apr. 8, 2020

(87) PCT Pub. No.: WO2019/073239
PCT Pub. Date: Apr. 18, 2019

(65) Prior Publication Data
US 2020/0390158 A1    Dec. 17, 2020

(30) Foreign Application Priority Data
Oct. 12, 2017   (GB) ..................................... 1716730

(51) Int. Cl.
*A24F 13/00*        (2006.01)
*A61M 15/06*        (2006.01)
(Continued)

(52) U.S. Cl.
CPC .......... *A61M 15/06* (2013.01); *A24F 40/465* (2020.01); *A24F 40/53* (2020.01); *A24F 40/60* (2020.01); *A24F 40/65* (2020.01); *A24F 40/10* (2020.01)

(58) Field of Classification Search
CPC ....................................................... A24F 47/00
(Continued)

(56) References Cited

U.S. PATENT DOCUMENTS 5,598,868 A    2/1997  Jakob et al.
5,649,554 A    7/1997  Sprinkel et al.
(Continued)

FOREIGN PATENT DOCUMENTS

CL    199600626 A1   4/1997
CN    101883596 A    11/2010
(Continued)

OTHER PUBLICATIONS

International Preliminary Report on Patentability for Application No. PCT/GB2018/052911, dated Apr. 23, 2020, 8 pages.
(Continued)

*Primary Examiner* — Phuong K Dinh
(74) *Attorney, Agent, or Firm* — Patterson, Thuente PA

(57) ABSTRACT

An electronic vapor provision system includes an inhaler component for generating vapor from a vapor precursor material, and a base unit to which the inhaler component may be selectively coupled and uncoupled; wherein the base unit is configured to establish an identifier for the inhaler component and, when the inhaler component is coupled to the base unit, to provide the inhaler component with an amount of consumable for use by the inhaler component for generating vapor for user inhalation when the inhaler component is uncoupled from the base unit; wherein the base unit is further configured to establish a record of the identifier for the inhaler component in association with an indication the consumable has been provided to the inhaler component.

20 Claims, 7 Drawing Sheets

(51) Int. Cl.
  *A24F 40/53* (2020.01)
  *A24F 40/65* (2020.01)
  *A24F 40/465* (2020.01)
  *A24F 40/60* (2020.01)
  *A24F 40/10* (2020.01)

(58) Field of Classification Search
  USPC .................................................. 131/328–329
  See application file for complete search history.

(56) References Cited

U.S. PATENT DOCUMENTS

| | | | |
|---|---|---|---|
| 8,464,726 | B2 | 6/2013 | Sebastian et al. |
| 10,660,368 | B2 | 5/2020 | Thorens |
| 10,758,686 | B2 | 9/2020 | Reevell |
| 11,357,936 | B2 | 6/2022 | Lipowicz |
| 2009/0283103 | A1 | 11/2009 | Nielsen et al. |
| 2013/0037041 | A1 | 2/2013 | Worm et al. |
| 2014/0107815 | A1 | 4/2014 | Lamothe |
| 2014/0305820 | A1 | 10/2014 | Xiang |
| 2015/0020825 | A1 | 1/2015 | Galloway et al. |
| 2015/0101606 | A1 | 4/2015 | White |
| 2015/0136158 | A1 | 5/2015 | Stevens et al. |
| 2015/0196053 | A1 | 7/2015 | Liu |
| 2015/0208729 | A1 | 7/2015 | Monsees et al. |
| 2015/0224268 | A1 | 8/2015 | Henry et al. |
| 2015/0272219 | A1 | 10/2015 | Hatrick et al. |
| 2015/0320116 | A1 | 11/2015 | Bleloch et al. |
| 2015/0327596 | A1 | 11/2015 | Alarcon et al. |
| 2015/0332379 | A1 | 11/2015 | Alarcon |
| 2016/0204637 | A1* | 7/2016 | Alarcon .................. A24F 40/95 320/114 |
| 2016/0206000 | A1 | 7/2016 | Lord et al. |
| 2016/0211693 | A1 | 7/2016 | Stevens et al. |
| 2017/0196269 | A1 | 7/2017 | Bernauer et al. |
| 2017/0258136 | A1 | 9/2017 | Hawes et al. |
| 2018/0043114 | A1 | 2/2018 | Bowen et al. |
| 2018/0154103 | A1 | 6/2018 | Davis |
| 2020/0113227 | A1* | 4/2020 | Mclaughlin ............ A24D 3/0225 |

FOREIGN PATENT DOCUMENTS

| | | |
|---|---|---|
| CN | 104619202 A | 5/2015 |
| CN | 204334029 U | 5/2015 |
| CN | 104983077 A | 10/2015 |
| CN | 105792687 A | 7/2016 |
| CN | 106455724 A | 2/2017 |
| CN | 206341938 U | 7/2017 |
| CN | 206403198 U | 8/2017 |
| EP | 2996504 A1 | 3/2016 |
| JP | 2005198538 A | 7/2005 |
| JP | 2006320286 A | 11/2006 |
| JP | 2013137789 A | 7/2013 |
| JP | 2014500017 A | 1/2014 |
| JP | 2014532435 A | 12/2014 |
| JP | 2015507476 A | 3/2015 |
| JP | 2015531601 A | 11/2015 |
| JP | 2016525341 A | 8/2016 |
| JP | 2017506915 A | 3/2017 |
| JP | 2017509339 A | 4/2017 |
| JP | 2017516269 A | 6/2017 |
| RU | 2517125 C2 | 5/2014 |
| RU | 2527351 C2 | 8/2014 |
| RU | 2618436 C2 | 5/2017 |
| RU | 2632634 C2 | 10/2017 |
| WO | WO-9527411 A1 | 10/1995 |
| WO | WO-2004011067 A1 | 2/2004 |
| WO | 2009069518 A1 | 6/2009 |
| WO | WO-2014048745 A1 | 4/2014 |
| WO | WO-2015140554 A1 | 9/2015 |
| WO | WO-2015158482 A1 | 10/2015 |
| WO | WO-2015177253 A1 | 11/2015 |
| WO | WO-2015177294 A1 | 11/2015 |
| WO | WO-2016062777 A1 | 4/2016 |
| WO | WO-2016198266 A1 | 12/2016 |

OTHER PUBLICATIONS

International Preliminary Report on Patentability for Application No. PCT/GB2018/052912, dated Apr. 23, 2020, 8 pages.
International Search Report and Written Opinion for Application No. PCT/GB2018/052912, dated Jan. 18, 2019, 10 pages.
International Search Report and Written Opinion for Application No. PCT/GB2018/052911, dated Jan. 18, 2019, 13 pages.
Notice of Reasons for Rejection for Japanese Application No. 2020-518790, dated Jul. 6, 2021, 12 pages.
Office Action dated May 12, 2022 for Colombian Application No. NC2020/0005749, 8 pages.
Office Action for Canadian Application No. 3,078,859, dated Jun. 7, 2021, 8 pages.
Office Action for Japanese Application No. 2020-518790, dated Jun. 25, 2021, 29 pages.
Office Action for Japanese Application No. 2020-520247, dated Jul. 6, 2021, 14 pages.
Office Action for Russian Application No. 2020112259, dated Feb. 3, 2021, 10 pages.
Search Report for Russian Application No. 2020112315 dated Nov. 17, 2020, 2 pages.
"Office Action received for Chinese Patent Application No. 2018800663612, dated Apr. 22, 2022".

\* cited by examiner

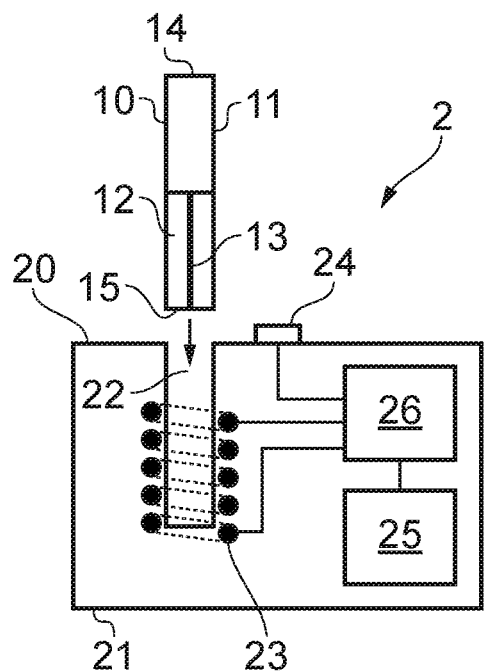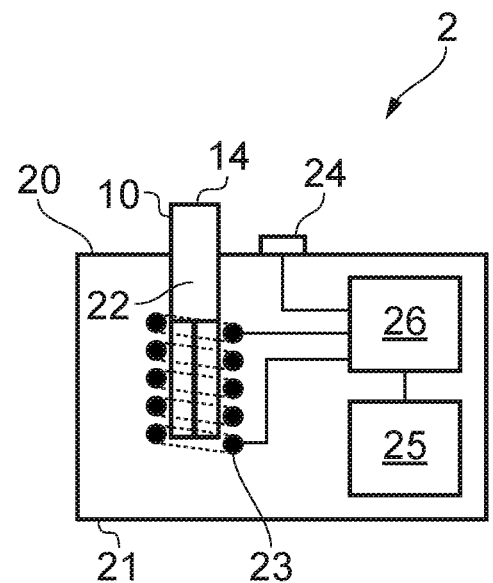
FIG. 1A    FIG. 1B
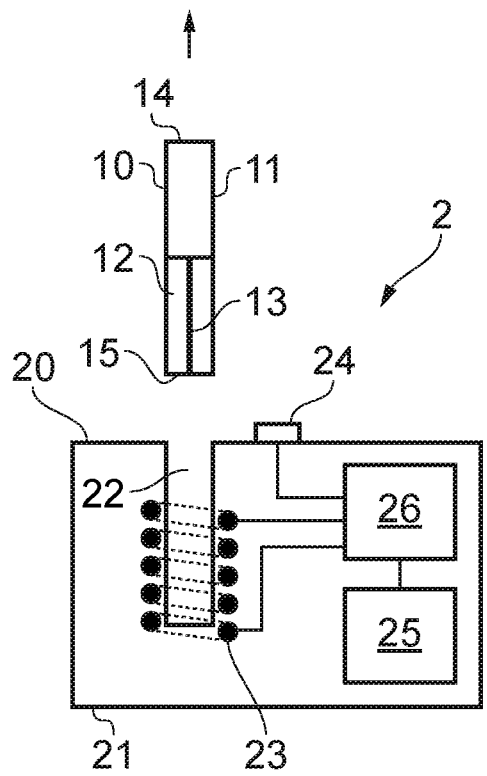
FIG. 1C

AEROSOL PROVISION SYSTEMS

PRIORITY CLAIM

The present application is a National Phase entry of PCT Application No. PCT/GB2018/052912, filed Oct. 11, 2018, which claims priority from GB Patent Application No. 1716730.5, filed Oct. 12, 2017, each of which is hereby fully incorporated herein by reference.

FIELD

The present disclosure relates to vapor provision systems such as nicotine delivery systems (e.g. electronic cigarettes and the like).

BACKGROUND

Conventional vapor provision systems for generating a vapor for user inhalation, such as electronic cigarettes (e-cigarettes), typically include the following main components:

(i) a vapor precursor material from which the vapor is generated;

(ii) a vaporizer for generating vapor from the vapor precursor material in a vapor generation region, e.g. through heat vaporization;

(iii) control circuitry for controlling the operation of the vaporizer, e.g. including a sensor for activating the vaporizer, such as a button or puff sensor, and also in many cases a microcontroller for providing additional functionality; and (iv) a power supply, typically a rechargeable battery, for driving the vaporizer.

During use, a user inhales on a vapor outlet (mouthpiece) for the system while electrical power is supplied to the vaporizer to vaporize a portion of the vapor precursor material. Air is drawn into the device through inlet holes and into the vapor generation region where it mixes with the vaporized precursor material and forms a condensation aerosol. The mixture of air and vapor/condensation aerosol is drawn along an outlet flow path from the vapor generation region to the mouthpiece for inhalation by the user.

Vapor provision systems often, though not always, comprise a modular assembly including both a reusable part and a replaceable cartridge part. Typically the replaceable cartridge part will comprise the vapor precursor material and the vaporizer and the reusable device part will comprise the power supply (rechargeable battery) and control circuitry. It will be appreciated these different parts may comprise further elements depending on functionality. For example, the reusable device part may comprise a user interface for receiving user configuration input and for displaying operating status characteristics, and the replaceable cartridge part may comprise a temperature sensor for helping to regulate the vaporization temperature.

Cartridges are electrically and mechanically coupled to a control unit for use, for example using a screw thread or bayonet fixing with appropriately engaging electrical contacts. When the vapor precursor material in a cartridge is exhausted, or the user wishes to switch to a different cartridge having a different vapor precursor material, a cartridge may be removed from the control unit and a replacement cartridge attached in its place.

Vapor provision systems are in some respects relatively complex devices which are often significantly larger than conventional cigarettes and can be costly to produce. In many cases this is warranted having regard to the desired functionality, for example in terms of operating features and capacity. However, the inventors have recognized there are also situations in which a simpler form of device may be preferred, for example to provide a relatively low-cost one-time use type of disposable device (e.g. lasting for a similar time to a conventional combustible cigarette) that may be made readily available for users who might not wish to carry a more conventional electronic cigarette, or whose usual device is out of power or has been forgotten. There are also users who would, at least on some occasions, prefer to use a vapor provision system which is more similar in size to a conventional combustible cigarette.

Various approaches are described which seek to help address or mitigate at least some of these issues.

SUMMARY

According to a first aspect of certain embodiments there is provided an electronic vapor provision system comprising: an inhaler component for generating vapor from a vapor precursor material, and a base unit to which the inhaler component may be selectively coupled and uncoupled; wherein the base unit is configured to establish an identifier for the inhaler component and, when the inhaler component is coupled to the base unit, to provide the inhaler component with an amount of consumable for use by the inhaler component for generating vapor for user inhalation when the inhaler component is uncoupled from the base unit; wherein the base unit is further configured to establish a record of the identifier for the inhaler component in association with an indication the consumable has been provided to the inhaler component.

According to another aspect of certain embodiments there is provided an inhaler component for generating vapor from a vapor precursor material for an electronic vapor provision system comprising the inhaler component and a base unit, wherein the base unit and the inhaler component may be selectively coupled and uncoupled; wherein the inhaler component is associated with an identifier that is provided to the base unit, and wherein the inhaler component is configured to receive an amount of consumable from the base unit when the inhaler component is coupled to the base unit and to generate vapor for user inhalation when the inhaler component is uncoupled from the base unit.

According to another aspect of certain embodiments there is provided a base unit for an electronic vapor provision system comprising the base unit and an inhaler component for generating vapor from a vapor precursor material, wherein the base unit and the inhaler component may be selectively coupled and uncoupled; wherein the base unit is configured to establish an identifier for an inhaler component coupled to the base unit and, when the inhaler component is coupled to the base unit, to provide the inhaler component with an amount of consumable for use by the inhaler component for generating vapor for user inhalation when the inhaler component is uncoupled from the base unit; wherein the base unit is further configured to establish a record of the identifier for the inhaler component in association with an indication the consumable has been provided to the inhaler component.

According to another aspect of certain embodiments there is provided a server configured to connect to a remote base unit of an electronic vapor provision system comprising the base unit and an inhaler component, wherein the base unit is configured to establish an identifier for the inhaler component and to provide the inhaler component with a consumable for use by the inhaler component for generating vapor for user inhalation when the inhaler component is uncoupled from the base unit, and wherein the server is configured to receive from the base unit an indication of a record of the identifier for the inhaler component in association with an indication the consumable has been provided by the base unit to the inhaler component.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which:

FIGS. 1A to 1C represent in highly schematic cross-section a vapor provision system in accordance with certain embodiments of the disclosure at different stages of use.

DETAILED DESCRIPTION

Figure 2:
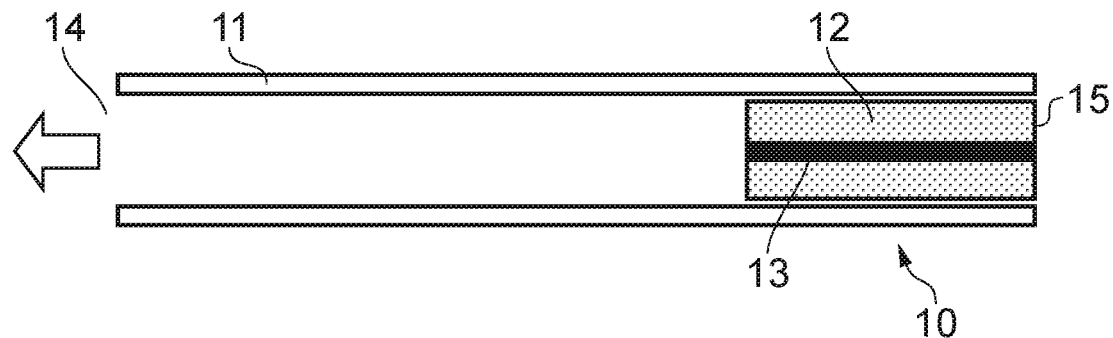
FIGS. 2 to 11 represent in highly schematic cross-section an inhaler component of a vapor provision system in accordance with certain embodiments of the disclosure.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to vapor provision systems, which may also be referred to as aerosol provision systems, such as e-cigarettes. Throughout the following description the term "e-cigarette" or "electronic cigarette" may sometimes be used; however, it will be appreciated this term may be used interchangeably with vapor (aerosol) provision system and electronic vapor (aerosol) provision system. Furthermore, and as is common in the technical field, the terms "vapor" and "aerosol", and related terms such as "vaporize" and "aerosolize", may also be used interchangeably.

FIGS. 1A to 1C represent in highly schematic cross-section a vapor provision system 2 in accordance with certain embodiments of the disclosure at different stages of use. The system 2 represented here comprises two main components, namely an inhaler component 10 and a base unit 20. As discussed further herein, the inhaler component 10 may be placed in (or in other embodiments on) the base unit 20 to prepare it for use (i.e. to initiate vapor generation), and then removed from the base unit for use (i.e. for user inhalation of the generated vapor).

The inhaler component 10 comprises a generally tubular housing 11 defining an air flow path between an air inlet 15 and a mouthpiece outlet 14. Within the housing 11 there is a source of vapor precursor material 12 arranged in/adjacent to the air flow path and a thermal store 13 in thermal contact with part of the vapor precursor material 12. There are various configurations which may be adopted for the arrangement of the vapor precursor material 12 and the thermal store 13 as discussed further below. For example, the vapor precursor material may comprise a solid, gel or foam material rather than, or in addition to, a liquid material. However, in this example the source of vapor precursor material comprises a liquid vapor precursor material retained by an absorbent/wadding material, e.g. organic cotton or other porous material, such as a fiberglass material or a porous metal or ceramic material, and the thermal store comprises a volume of metal, for example formed from a portion of sheet steel.

The tubular housing 11 in this example has a size which broadly corresponds with a conventional cigarette, for example having a length of around 100 mm and a diameter of around 7 mm. The internal diameter of the tubular housing may, for example, be around 5 mm. The housing 11 may in this example comprise a plastics material, but in other examples may comprise a card/paper material. Generally, the housing may be formed of any material, but there will typically be a desire for the housing to be made relatively cheaply given it will typically be intended to be a disposable item. The housing may be arranged to present an outer surface that mimics the appearance of a conventional cigarette, for example having a white color along the majority of its length with a brown section towards the mouthpiece outlet 14 representing a conventional cigarette filter section. However, it will be appreciated the aesthetic appearance of the inhaler component, as well as its specific shape, dimensions and material, are not of fundamental significance to the principles described herein.

As noted above, the vapor precursor material in this example comprises a vaporizable liquid retained by an material. In this example the wadding material comprises organic cotton, but in other examples the wadding material may comprise other absorbent materials, for example fiberglass, steel wool, paper, ceramic fibers, tobacco material and so forth. The liquid is of a type conventionally used in electronic cigarettes, for example comprising an amount of nicotine, e.g. around 3% nicotine, and a base liquid comprising around 50% glycerol and roughly equal measures of water and propylene glycol. The liquid may further comprise other components, such as a flavoring. In some examples a liquid having a relatively low vaporization temperature may be selected, for example, a liquid comprising a relatively large amount of ethanol or triacetin. It will be appreciated the specific liquid used in a given implementation may be a matter of user preference, for example by providing a range of inhaler components having vapor precursor materials with different characteristic, e.g. in terms of nicotine content and/or flavor, from which a user may select.

The thermal store in this example comprises a generally rectangular shape pressed from a sheet of steel and comprises, e.g. AISI type 430 or 409 steel, with dimensions of around 25 mm×3 mm×0.1 mm. However, other forms of thermal store may be adopted in other implementations, for example comprising different materials, e.g. conductive ceramic, other metals or alloys, e.g. comprising aluminum and/or iron and/or nickel, graphite and so on, and different shapes and sizes. For example, rather than having a generally flat shape, the thermal store in other implementations may have a tubular shape, for example in the form of a solid or hollow pin/rod. As discussed herein, heat in the thermal store may be used to heat and vaporize a portion of vapor precursor material for inhalation. A relatively large thermal mass for the thermal store will mean more vapor precursor material may be vaporized but can be expected to take longer to heat. On the other hand, a relatively small thermal mass for the thermal store will allow more rapid heating, but with less vapor generation before the thermal mass cools. Thus, for a given implementation, the thermal mass for the thermal store may be selected according to the desired properties in terms of balancing the rate of heating and the amount of vapor that can be vaporized for each use. As discussed further herein, the thermal store 13 in the example implementation represented in FIGS. 1A to 1C may be inductively heated by the base unit 20. In that regard the thermal store may also be referred to as a susceptor and comprise any material susceptible to inductive heating (e.g. a ferritic or martensitic steel). In other examples the thermal store 13 may be heated by the base unit 20 by means other than inductive heating, e.g. conductive and/or radiative heating, and in such cases the thermal store 13 need not comprise a material that is susceptible to inductive heating.

Turning now to the base unit 20, this is schematically represented in FIGS. 1A to 1C as having a generally rectangular box-like shape, but in practice the overall shape of the base unit is of no particular significance, and may, for example, be chosen according to a desired aesthetic appearance, for example, the base unit may equally be configured with an appearance which are generally similar to an ashtray or maybe generally flat, in the form of a mat. It will also be appreciated the base unit may not be a stand-alone device, but may be incorporated into another apparatus. For example, the base unit may be incorporated into a vehicle, for example with an appearance similar to a conventional cigarette lighter socket. It may be expected the base unit 20 will for many implementations comprise a relatively fixed installation, for example it may be fixed to a table or wall in a public place and be provided with mains power. However, in other implementations the base unit may be a portable device having an internal power supply and sized to allow it to be conveniently carried by a user.

The base unit 20 in this example comprises an outer housing 21 in which is defined a receiving zone 22 that is sized and shaped to receive at least a portion of the inhaler component 10, a power supply/rechargeable cell 25, control circuitry 26, an activation sensor 24, and an inductive coil 23.

In this example the receiving zone 22 is defined by a generally cylindrical recess in a top wall of the base unit 20. The cylindrical recess has a diameter which is a little larger than the diameter of the housing 10 of the inhaler component and a depth which allows the end of the inhaler component containing the susceptor 13 to be fully received in the cylindrical recess, as schematically represented in FIG. 1B. It will be appreciated this provides merely one example of a suitable size and shape for the receiving zone, and other arrangements may be adopted in other implementations. For example, in some implementations the receiving zone may not comprise any recess or opening in a surface of the base unit, but may simply comprise an area on an outer surface of the base unit against which the inhaler component 10 is placed.

The power supply 25 is arranged to provide operating power for the base unit 20. As noted above, for a portable base unit the power supply 25 may comprise a battery, e.g. a rechargeable lithium-ion battery. However in this example it is assumed the base unit 20 is intended for use in a generally fixed installation and receives external power, for example from a mains power supply. Thus, the power supply 25 in this example corresponds with a power circuit connected to an external mains power supply and arranged to convert the external mains power supply to a power supply suitable for operating the base unit, for example a 12 V DC power supply. It will, of course, be appreciated the particular nature of the power supply on which the base unit operates is not significant to the principles described herein. For example, in other implementations the base unit could be powered by a fuel cell or solar power (e.g. in the case of a base unit intended for outside use, such as in the vicinity of a bus stop).

The control circuitry 26 is configured to control the operation of the base unit 20 to provide the functionality described herein in accordance with embodiments of the disclosure. The control circuitry (processor circuitry) may comprise various sub-units/sub-circuits for providing this functionality and may be implemented as a number of discrete hardware elements and/or as appropriately configured functions of the control circuitry. Thus the control circuitry may comprise circuitry which is suitably configured/programmed to provide the desired functionality using conventional programming/configuration techniques for operating electronic devices. It will be appreciated the functionality of the control circuitry 26 can be provided in various different ways, for example using one or more suitably programmed programmable computer(s), or one or more suitably configured application-specific integrated circuit(s)/circuitry/chip(s)/chipset(s).

The inductive heater coil 23 is arranged so as to inductively heat the susceptor 13 in an inhaler component received in the receiving zone 22 when the inductive heater coil 23 is activated by the control circuitry. Thus, in the configuration of FIGS. 1A to 1C, the inductive heater coil comprises a helical coil wound around the cylindrical recess comprising the receiving zone over a portion that surrounds the susceptor 13 when the inhaler component is in the receiving zone. Thus, when the inhaler component 10 is received in the receiving zone 22 and the inductive heater coil 23 is driven to induce current in the susceptor 13, the susceptor is heated. The operating characteristics of the inductive heater coil 23, for example in terms of the number of turns, current and frequency of operation, may be selected having regard to the well understood principles of inductive heating taking account of the particular susceptor geometry adopted in a given implementation. In this regard, the inductive heater coil may, for example, be designed so as to heat the susceptor/thermal store in the inhaler component to a temperature of around 200° on a timescale on the order of a few seconds.

The activation sensor 24 is configured to provide an indication to the control circuit 26 when it should apply current to the inductive heater coil 23. In effect, the role of the activation sensor is to indicate to the control circuitry when an inhaler component currently in the receiving zone is about to be removed for use so that the control circuitry 26 should drive the inductive coil to heat the susceptor/thermal store in the inhaler component so that it is ready for use. The activation sensor 24 may be based on a range of different technologies in different implementations. For example, in some cases the activation sensor may comprise a motion sensor configured to detect movement of the inhalation component as a user starts to withdraw the inhalation component from the receiving zone. In some other cases the activation sensor may comprise a proximity sensor configured to detect the approach of a user's hand when the user is about to withdraw the inhaler component from the receiving zone. In yet other cases, the activation sensor may comprise a switch which is manually activated by a user to indicate they are about to withdraw the inhalation opponent from the receiving zone. In yet other cases, the activation sensor may be configured to simply detect when an inhaler component is inserted into the receiving zone, such that the inductive heater coil is activated whenever an inhaler component is placed in the receiving zone. Regardless of the specific manner in which the activation sensor is configured to detect when the control circuitry should drive the inductive heating coil 23, it may be implemented having regard to conventional sensing techniques. That is to say, it may be based on conventional techniques (e.g. using capacitive or optical sensing technologies for detecting the approach, presence or movement of an object according to the implementation at hand, or a conventional mechanical switch for manual activation). In some implementations the base unit might not comprise an activation sensor, and instead the induction coil may instead be permanently driven so that whenever an inhaler component is inserted in the base unit it is inductively heated. In another example, the base unit may be configured to receive the inhaler component in a first position, and then when a user moves the inhaler component to a second position (e.g. pushing down against a spring force or simply repositioning the inhaler component relative to the base unit), the inductive heating coil may be activated to heat the thermal store. In one example, the inhaler component may be configured to "pop up" after a given amount of time of heating, e.g. based on a timer or thermally responsive latch releasing a spring force, to indicate when the thermal store has been sufficiently heated for use. In some cases the base unit may comprise a second coil for detecting the motion of the susceptor/heat store as it starts to be removed from the base unit and the inductive heating coil driven accordingly.

Having discussed the overall structure and configuration of the vapor provision system 2 represented in FIGS. 1A, 1B and 1C, an example use of the system 2 will now be described. In this regard it is assumed FIG. 1A schematically represents a situation in which an un-used inhaler component is about to be used. Thus, in FIG. 1A the inhaler component 10 is shown on approach to the receiving zone 22 of the base unit 20. At this stage the susceptor/heat store 13 in the un-used inhaler component 10 is cold (i.e. at ambient temperature).

FIG. 1B shows the inhaler component 10 when it is received in the receiving zone 22 of the base unit 20. As discussed above, in this arrangement, the inductive heater coil 23 in the base unit 20 surrounds the susceptor 13 in the inhaler component 10. While the inhaler component 10 is located in the receiving zone as represented in FIG. 1B, the activation sensor 24 detects that the susceptor 13 in the inhaler component should be heated because it is about to be removed for use. As noted above, this detection may be based on different sensor technologies according to the implementation at hand. In this example it is assumed the activation sensor 24 is a motion sensor configured to detect motion of the inhaler component when a user starts to withdraw the inhaler component for use.

When the activation sensor 24 determines the susceptor 13 in the inhaler component should be heated, a signal is passed to the control circuitry 26, in response to which the control circuitry applies a drive signal to the inductive heating coil 23 by appropriately directing power from the power supply 25 to the coil. The application of a drive signal to the inductive heater coil induces currents in the susceptor 13, thereby heating the susceptor. In this example the inductive heater coil 23 is configured to heat the susceptor to a temperature of around 200° within two seconds. It will be appreciated the characteristics of the drive signal applied to the inductive heater coil 23 to achieve this rate of heating will depend on the susceptibility of the susceptor to induced currents and its thermal mass (i.e. the size of the thermal store 13). However, as noted above, the operation of the inductive heater coil may be in accordance with conventional inductive heater techniques.

In this example in which the inductive heating is triggered by the activation sensor 24 detecting the inhaler component 10 is being withdrawn from (i.e. starts moving away from) the receiving zone, a user of the vapor provision system 2 may be made aware of a need to withdraw the inhaler component 10 from the receiving zone relatively slowly to allow time for the susceptor to be heated as it is withdrawn. In some cases an indicator, for example a light, may be provided to indicate when the induction heater coil 23 is being driven. Thus, when the control circuitry determines that sufficient energy has been transferred to the susceptor 13 in the inhaler component (e.g. after a predetermined amount of time of driving the induction heating coil), the indicator light may switch off. Thus, when a user starts to withdraw the inhaler component 10 from the receiving zone they will see the indicator light illuminate and understand they should delay withdrawing the inhaler component until after the indicator light goes out. If there is a concern for a given implementation that an approach based on triggering the heater coil in response to the base unit determining when the inhaler component starts to be withdrawn will not give sufficient time to heat the susceptor without requiring a delay which may frustrate a user, a different activation sensor approach may be adopted. For example, a proximity sensor approach based on detection of a user's hand approaching the base unit as discussed above may be used instead. In this case the activation of the heating coil 23 can begin before the user starts to remove the inhaler component from the base unit, thereby helping reduce any user-perceived delay.

FIG. 1C schematically represents the inhaler component 10 having been removed from the base unit 20 after the susceptor/thermal store 13 has been heated by the inductive coil 23. At this stage the inhaler component 10 is ready for user inhalation in that a user may inhale on the mouthpiece end 14 to draw air in through the inlet 15 and along the airflow path defined by the housing 11. As the user is doing this, the heat in the thermal store 13 vaporizes a portion of the vapor precursor material 12 through thermal conduction so the resulting vapor becomes entrained in the airflow through the inhaler component and is inhaled by a user through the mouthpiece 14. In some configurations the organic cotton holding the liquid air vapor precursor material may be sufficiently loose that air can be drawn through the wadding, and in some other configurations an air channel may be provided by a passageway through the wadding in the vicinity of the susceptor to allow air to be drawn through the inhaler component primarily in the region where the vapor is being generated by the thermal store 13.

Having taken a puff on the inhaler component and inhaled a portion of the vapor, the user may in some cases continue to hold the inhaler component ready for a second puff in the event the thermal store has sufficient heat capacity to retain a temperature which is sufficient to continue to vaporize enough vapor precursor material for a second (and potentially further) puffs. In other cases the thermal store may be sufficient to provide only one puff, so that when a user has taken a puff, the inhaler component may be returned to the receiving zone ready to be re-heated for the next puff in the same way as discussed above. A user may continue to puff on the inhaler component, reheating as necessary, until the vapor precursor material is exhausted. After this time the inhaler component may be discarded and a new inhaler component used, although in principle the inhaler component may also be refilled. For example, it may be dipped in a pool of liquid vapor precursor material so that the cotton wadding absorbs a portion of the liquid to in effect refill the inhaler component with vapor precursor material for further use. In some examples a pool/reservoir of vapor precursor material may be provided within the base unit such that when an inhaler component is received in the receiving zone, a part of the inhaler component, for example an end, is in contact with the reservoir of vapor precursor material. Thus, not only does the base unit provide the inhaler component with heat to vaporize the vapor precursor material, the base unit may also provide the inhaler component with the vapor precursor material itself. In that sense the inhaler components may be initially supplied without any vapor precursor material. Furthermore, in some cases the inhaler component may be configured to absorb an amount of liquid corresponding to a single puff which may be vaporized while the inhaler component is still in the receiving zone of the base unit, with the vaporized material remaining in the inhaler component until it is withdrawn and inhaled by a user.

It may be expected one use scenario would be for a base unit to be provided in a public space, for example in a restaurant, bar or area where people frequently wait, such as a bus stop, and users may simply buy individual or packets of inhaler components to be used on a disposable basis in conjunction with such "public" base units. For example, the base unit may be provided by a manufacturer/supplier of the inhaler components. In that regard, the inhaler components and base units may be configured only to operate together, for example by requiring a specific shape for the inhaler component to match a specific shape of the base unit or using other identification means, for example an RFID tag in each inhaler component to identify it as an inhaler component which may be used with the relevant base unit(s). This approach therefore provides users with the ability to inhale vapor of the kind provided by electronic cigarettes without needing a complete standalone device (i.e. a device with a battery and control electronics of their own). This may be desired for a number of reasons. For example a user may simply not wish to carry a bulkier standalone device. A user may have their own device, but have forgotten to take it with them, and so may wish to purchase a pack of the disposable inhaler components for use with a public base unit in the interim. In yet another scenario, a user may have their own electronic cigarette, but simply want to try a new flavor provided as a disposable inhaler component of the kind described above, for example by way of a sample test.

FIG. 2 schematically represents in cross-section view the inhaler component discussed above with reference to FIGS. 1A to 1C.

Figure 3:
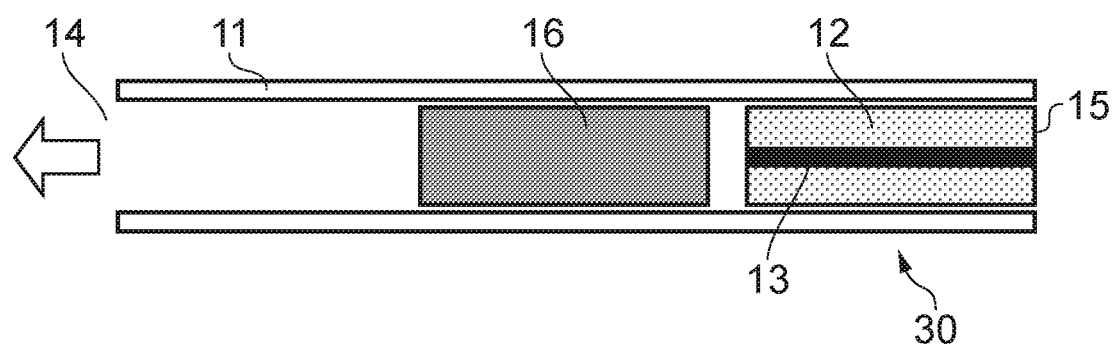

FIG. 3 represents in schematic cross-section view an inhaler component 30 that is a variation of the inhaler component 10 discussed above with reference to FIGS. 1A to 1C and shown in FIG. 2. Elements of the inhaler component 30 represented in FIG. 3 which are functionally similar to, and will be understood from, corresponding elements of the inhaler component 10 represented in FIG. 2 are identified with corresponding reference numerals and are not discussed again in the interests of brevity. The inhaler component 3 differs from the inhaler component represented in FIG. 2 by the addition of a portion of tobacco 16 within the housing 11. The tobacco portion 16 may comprise a section of loose cut tobacco arranged on a downstream side of the vapor precursor material 12 and thermal store 13 (i.e. between the vapor precursor material and the mouthpiece) so that vapor generated from the vapor precursor material is drawn through the tobacco 16 before inhalation. This can help provide a user with additional flavor characteristics that may be desired in some cases. The inhaler component 30 of FIG. 3 may be used in conjunction with a base unit corresponding to that used with the inhaler component 10 of FIG. 2 and discussed above.

Figure 4:
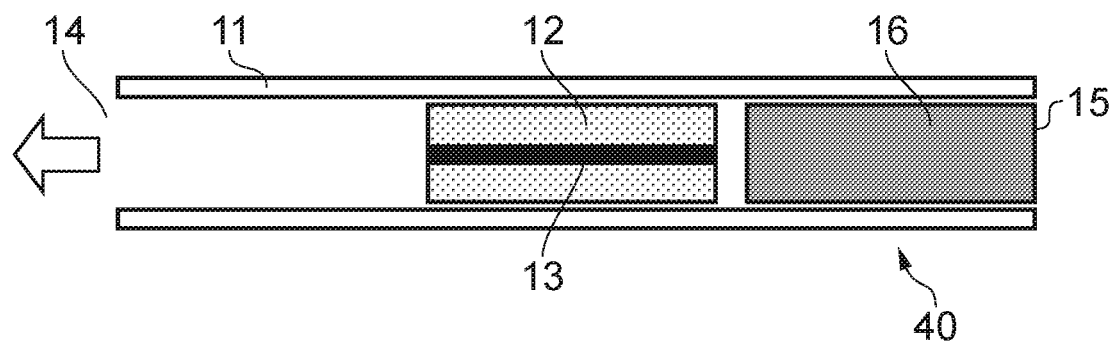

FIG. 4 represents in schematic cross-section view an inhaler component 40 that is another variation of the inhaler component 10 discussed above with reference to FIGS. 1A to 1C and shown in FIG. 2. Elements of the inhaler component 40 represented in FIG. 4 which are functionally similar to, and will be understood from, corresponding elements of the inhaler component 10 represented in FIG. 2 are identified with corresponding reference numerals and are not discussed again in the interests of brevity. The inhaler component represented in FIG. 4 differs from the inhaler component represented in FIG. 2 by the addition of a portion of tobacco 16 within the housing 11. The tobacco portion 16 is arranged on an upstream side of the vapor precursor material 12 and thermal store 13 (i.e. the vapor precursor material is between the tobacco portion and the mouthpiece) so that air entering the inhaler component is drawn through the tobacco 16 before passing the vapor precursor material. This can help provide a user with additional flavor characteristics that may be desired in some cases. The inhaler component 40 of FIG. 4 may be used in conjunction with a base unit corresponding to that used with the inhaler component 10 of FIG. 2 and discussed above, albeit with the cylindrical recess defined by the receiving zone being made sufficiently deep for the portion of the inhaler component having the susceptor to be located adjacent the inductive heating coil in the base unit.

Figure 5:
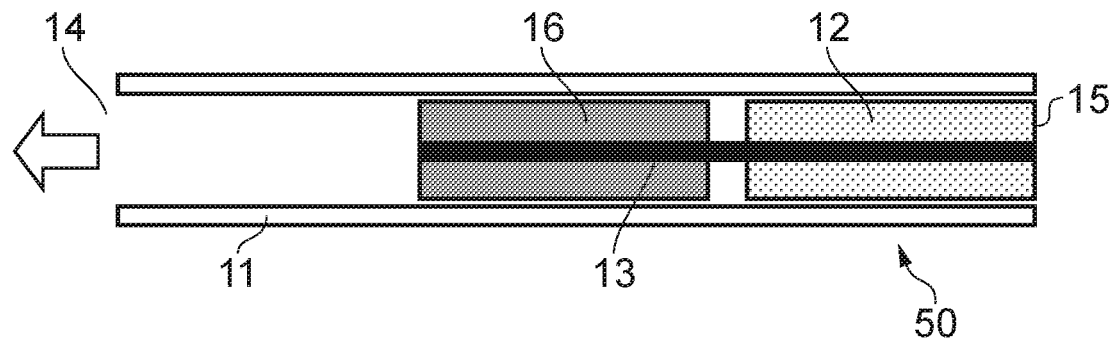

FIG. 5 represents in schematic cross-section view an inhaler component 50 that is a variation of the inhaler component 30 discussed above and shown in FIG. 3. Elements of the inhaler component 50 represented in FIG. 5 which are functionally similar to, and will be understood from, corresponding elements of the inhaler component 30 represented in FIG. 3 are identified with corresponding reference numerals and are not discussed again in the interests of brevity. The inhaler component represented in FIG. 5 differs from the inhaler component represented in FIG. 3 by virtue of the thermal store/susceptor 13 having an extent that places it in thermal contact with both the liquid vapor precursor material 12 and the tobacco portion 16. Accordingly, in use the tobacco portion 16, as well as the vapor precursor material 12 are both heated by the thermal store. In that sense the tobacco portion 16 may itself be considered a part of the inhaler component's vapor precursor material (i.e., FIG. 5 represents an example in which the vapor precursor material comprises both a liquid and a solid). In a variation on this approach, the liquid vapor precursor material and the tobacco portion may be associated with separate susceptors (as opposed to a single susceptor spanning both of them) which can be separately heated by the base unit. The inhaler component 50 of FIG. 5 may be used in conjunction with a base unit corresponding to that used with the inhaler component 10 of FIG. 2 and discussed above, albeit with the cylindrical recess defined by the receiving zone and the induction heating coil being made sufficiently large for the portion of the inhaler component having the susceptor to be located adjacent the inductive heating coil(s) in the base unit.

Figure 6:
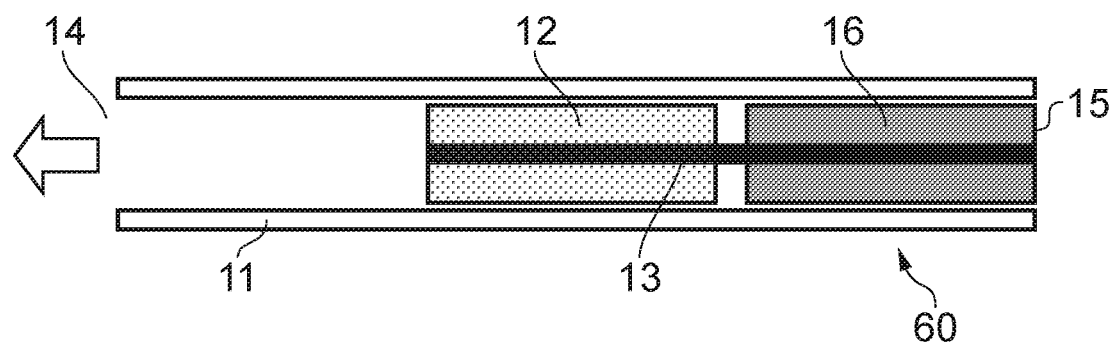

FIG. 6 represents in schematic cross-section view an inhaler component 60 that is a variation of the inhaler component 50 discussed above and shown in FIG. 5. Elements of the inhaler component 60 represented in FIG. 6 which are functionally similar to, and will be understood from, corresponding elements of the inhaler component 50 represented in FIG. 5 are identified with corresponding reference numerals and are not discussed again in the interests of brevity. The inhaler component represented in FIG. 6 differs from the inhaler component represented in FIG. 5 by virtue of the liquid vapor precursor material 12 and the tobacco portion (solid vapor precursor material) 16 being swapped in their relative positions along the airflow path between the air inlet 15 and the mouthpiece outlet 14. The inhaler component 60 of FIG. 6 may be used in conjunction with a base unit corresponding to that used with the inhaler component 10 of FIG. 2 and discussed above, albeit with the cylindrical recess defined by the receiving zone and the induction heating coil being made sufficiently large for the portion of the inhaler component having the susceptor to be located adjacent the inductive heating coil(s) in the base unit.

Figure 7:
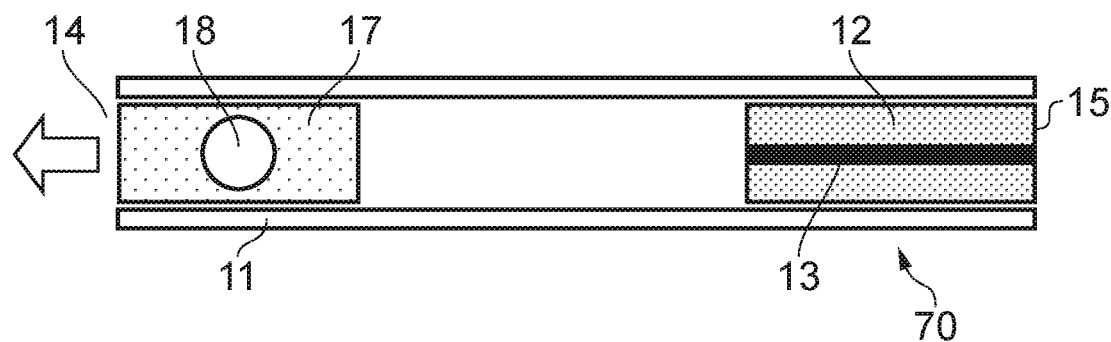

FIG. 7 represents in schematic cross-section view an inhaler component 70 that is a variation of the inhaler component 10 discussed above with reference to FIGS. 1A to 1C and shown in FIG. 2. Elements of the inhaler component 70 represented in FIG. 7 which are functionally similar to, and will be understood from, corresponding elements of the inhaler component 10 represented in FIG. 2 are identified with corresponding reference numerals and are not discussed again in the interests of brevity. The inhaler component represented in FIG. 7 differs from the inhaler component represented in FIG. 2 by the addition of a filter section 17 within the airflow path adjacent the mouthpiece opening 15. The filter section 17 may, for example, comprise a filter material of the type used in any conventional cigarette, e.g. cellulose acetate. Furthermore, the filter section 17 includes a flavor capsule 18 which may be selectively broken by a user to allow flavorant within the capsule to absorb within the filter and impart flavor characteristic to the vapor provided by the inhaler component. For example, the flavor capsule 18 may comprise a breakable shell containing a liquid containing menthol, or other, flavorant. In this regard, the flavor capsule 18 may correspond, e.g. in terms of its material structure and contents, with the types of flavor capsules commonly used in conjunction with conventional cigarettes. The inhaler component 70 of FIG. 7 may be used in conjunction with a base unit corresponding to that used with the inhaler component 10 of FIG. 2 and discussed above. More generally, it will be appreciated the inhaler component may be provided with other means for modifying the organoleptic properties of the output from the inhaler component, e.g. by filtering or adding flavorings.

It will further be appreciated there are various different ways in which the vapor precursor material and thermal store can be provided in addition to approaches based on liquid-soaked wadding and a planar susceptor such as in some of the example discussed above. Some alternative configurations are schematically represented in FIGS. 8 to 10.

Figure 8:
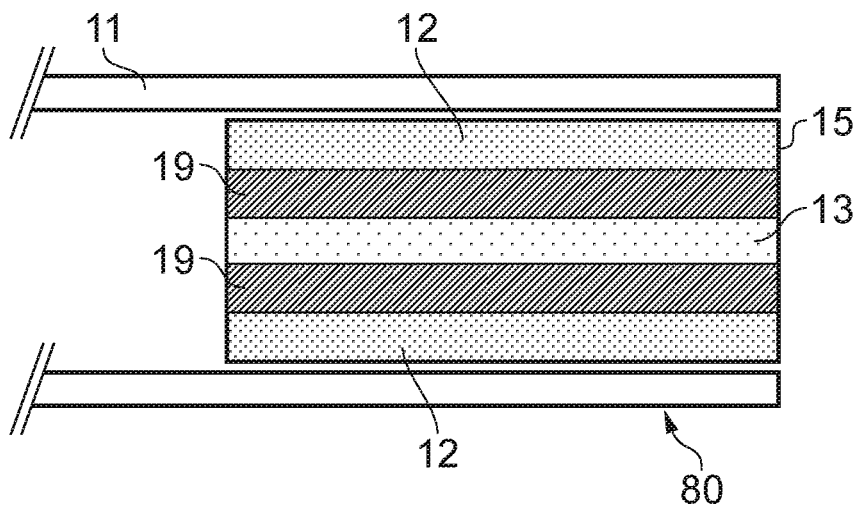

FIG. 8 represents in schematic cross-section view an inhaler component 80 that is a variation of the inhaler component 10 discussed above with reference to FIGS. 1A to 1C and shown in FIG. 2. Elements of the inhaler component 80 represented in FIG. 8 which are functionally similar to, and will be understood from, corresponding elements of the inhaler component 10 represented in FIG. 2 are identified with corresponding reference numerals. Only a portion of the inhaler component 80 in the vicinity of the inlet 15 is represented in FIG. 8, it being understood the remainder of the inhaler component may be provided in line with any of the other examples discussed herein. The inhaler component 80 represented in FIG. 8 differs from the inhaler component 10 represented in FIG. 2 by the manner in which the liquid vapor precursor material is fed to the susceptor/thermal store for heating. In the example described above, the vapor precursor material is stored in a cotton wadding which is generally in proximity to the thermal store. However, in the example of FIG. 8, the liquid vapor precursor material 12 is stored in an annular reservoir around the inside of the tube 11 and a wicking element 19, in this example comprising ceramic fibers, is arranged to draw the liquid vapor precursor material to the susceptor 13 for vaporization. The liquid vapor precursor material may be stored in an annular wadding material, e.g. of the kind discussed above with reference to the configuration of FIG. 2, or may comprise free liquid retained in an annular walled chamber into which the wicking element extends. In this regard, the arrangement of FIG. 8 may be considered to comprise a relatively high-porosity region for storing the bulk of the liquid vapor precursor material and a wicking element with a lower porosity for controlling the flow of liquid to the susceptor at a desired rate. It will be appreciated the wicking element may comprise other materials and forms, for example a porous rather than fibrous material, and may comprise a ceramic, metallic or any other suitable material, for example fiberglass. More generally, any material able to withstand the heat of the susceptor and capable of wicking the liquid vapor precursor material to the susceptor may be used. The inhaler component 80 of FIG. 8 may be used in conjunction with a base unit corresponding to that used with the inhaler component 10 of FIG. 2 and discussed above.

Figure 9:
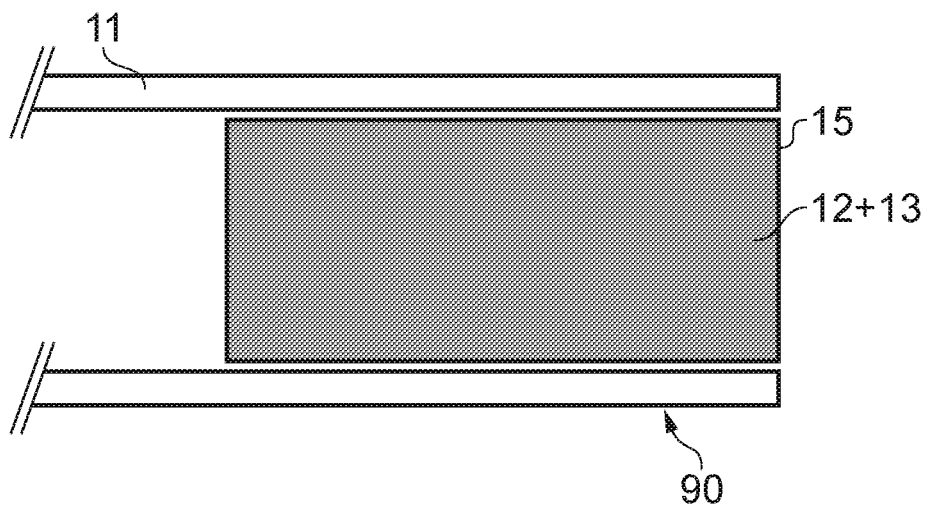

FIG. 9 represents in schematic cross-section view an inhaler component 90 which is yet another variation of the inhaler component 10 discussed above with reference to FIGS. 1A to 1C and shown in FIG. 2. Elements of the inhaler component 90 represented in FIG. 9 which are functionally similar to, and will be understood from, corresponding elements of the inhaler component 10 represented in FIG. 2 are identified with corresponding reference numerals. As for FIG. 8, only a portion of the inhaler component 90 in the vicinity of the inlet 15 is represented in FIG. 9, it being understood the remainder of the inhaler component may be provided in line with any of the examples discussed above. The inhaler component 90 represented in FIG. 9 differs from the inhaler component 10 represented in FIG. 2 by the arrangement of the thermal store/susceptor 13 and the vapor precursor material 12. In particular, the thermal store/susceptor 13 in the example of FIG. 9 comprises a fibrous metallic material, for example a wire wool/steel wool, and the vapor precursor material 12 comprises a gel coating on the fibers comprising the susceptor 13. This may be formed, for example, by simply dipping the fibrous susceptor 13 into a liquid form of the vapor precursor material which subsequently dries/cools to form a gel. The inhaler component 90 of FIG. 9 may be used in conjunction with a base unit corresponding to that used with the inhaler component 10 of FIG. 2 and discussed above. Thus, when the inhaler component 90 is received in the receiving zone of the base unit, current may be induced in the fibrous susceptor 13 causing it to heat, and so vaporize the gel vapor precursor material 12 coating the fibers comprising the susceptor 13 for inhalation when the inhaler component is withdrawn from the base unit.

Figure 10:
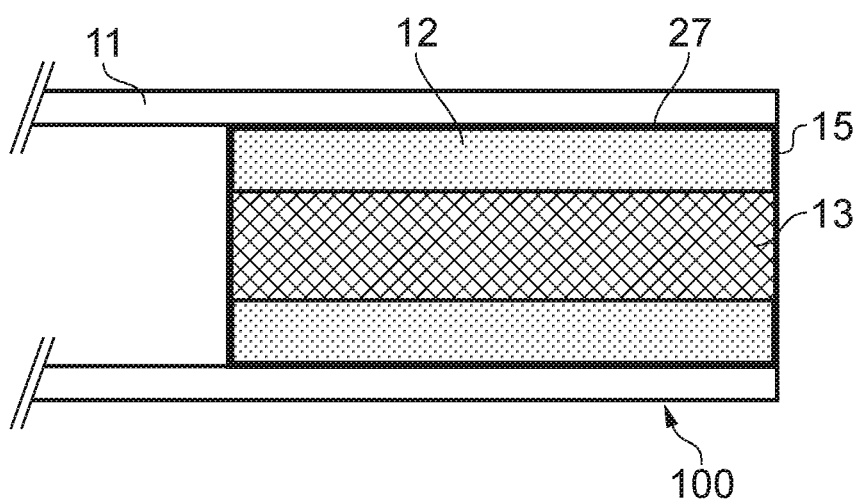

FIG. 10 represents in schematic cross-section view an inhaler component 100 which is yet another variation of the inhaler component 10 discussed above with reference to FIGS. 1A to 1C and shown in FIG. 2. Elements of the inhaler component 100 represented in FIG. 10 which are functionally similar to, and will be understood from, corresponding elements of the inhaler component 10 represented in FIG. 2 are identified with corresponding reference numerals. As for FIGS. 8 and 9, only a portion of the inhaler component 100 in the vicinity of the inlet 15 end of the inhaler component is represented in FIG. 10, it being understood the remainder of the inhaler component may correspond with any of the other examples discussed herein. The inhaler component 100 represented in FIG. 10 again differs from the inhaler component 10 represented in FIG. 2 by the arrangement of the thermal store/susceptor 13 and the vapor precursor material 12. In particular, in the arrangement represented in FIG. 10, liquid vapor precursor material 12 is stored in an annular walled chamber 27 rather than in a matrix of cotton wadding. The walled chamber 27 may, for example, comprise a generally tubular insert for locating within the tube housing 11 of the inhaler component 100, as schematically represented in FIG. 10, but in other implementations may be integrally formed with the housing 11. The susceptor in FIG. 10 comprises a generally planar metallic mesh (or other porous structure), e.g. a sintered metal fiber material generally in the form of a sheet. At least one edge of the susceptor extends into a corresponding slot in an inner wall of the chamber 27, thereby allowing the susceptor to wick liquid 12 from within the chamber 27 and so become wet. During use, the susceptor 13 is heated by an induction coil in a base unit of the kind discussed above so that liquid is vaporized from the surface of the susceptor 13 for inhalation by a user. Liquid which is vaporized from the susceptor 13 is replenished by wicking from the liquid in the surrounding chamber due to the porosity of the susceptor material itself. As already noted, it will be appreciated the specific size and shape of the susceptor 13 is not critical, but in the example of FIG. 10 it is a generally rectangular shape comprising sintered fibers of steel and has dimensions of around 25 mm×3.5 mm by 1 mm.

Figure 11:
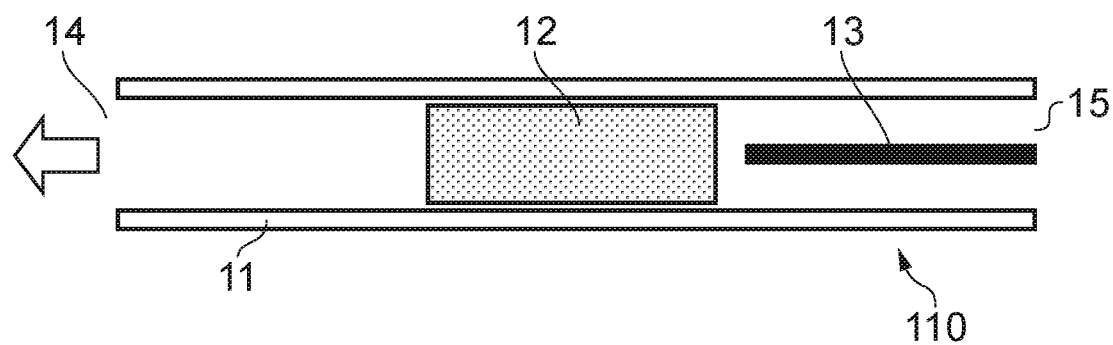

FIG. 11 represents in schematic cross-section view an inhaler component 110 that represents yet another variation of the inhaler component 10 discussed above with reference to FIGS. 1A to 1C and shown in FIG. 2. Elements of the inhaler component 110 represented in FIG. 11 which are functionally similar to, and will be understood from, corresponding elements of the inhaler component 10 represented in FIG. 2 are identified with corresponding reference numerals. The inhaler component 110 represented in FIG. 11 differs from the inhaler component represented in FIG. 2 in that the vapor precursor material 12 is not in direct thermal contact with the susceptor/thermal store 13, but is located upstream (i.e. between the susceptor/thermal store 13 and the mouthpiece outlet 14). Thus, in use, the susceptor is heated, for example using a base unit of the kind discussed above, and when a user inhales on the mouthpiece end 14, air is drawn through the air inlet and into the inhaler component 110 where it is heated by heat in the thermal store 13 so the heated air is drawn through/over the vapor precursor material to generate the vapor for inhalation. This configuration may in some respects be considered to correspond to a puff activated device in that when a user is not drawing air through the inhaler component 110 there is no (or at least significantly less) heat transferred to the vapor precursor material, and so less vaporization when the device is not being puffed. In another implementation, the inhaler component may be arranged so that the thermal store may be moved relative to the vapor precursor material so that these two elements may be brought into alignment/proximity to generate vapor, and removed from alignment/proximity to in effect turn off vapor generation. In this case the relative movement may be driven by user inhalation, for example with one or other of the thermal store or the vapor precursor material being moved by air flow in the inhaler component has a user draws on the inhaler component mouthpiece. In yet another implementation, a region surrounding the thermal store may be closed by a flap which is opened when a user inhales on the inhaler component. Thus, the area surrounding the inhaler may in effect be a closed space from which vapor cannot escape until a user inhales on the device to open the flap and draw out the vapor.

It will of course be appreciated the features of the various embodiments of the disclosure described herein can be combined. For example, a filter and flavor capsule of the kind represented in FIG. 7 can be provided for any of the configurations represented in FIGS. 2 to 6 and 8 to 11. Similarly a tobacco portion of the kind represented in FIGS. 3 to 6 can be included in any of the configurations represented in FIGS. 8 to 11. Furthermore, any of the vapor precursor material and thermal store configurations represented in FIGS. 8 to 11 may be used in conjunction with any of the arrangements set out in FIGS. 2 to 7. More generally, it will be appreciated there are a wide range of implementations that may be adopted in line with the underlying principle of using a base unit to provide energy to heat a thermal store for vaporizing a vapor precursor material in an inhaler component which is withdrawn from the base unit for use.

Furthermore, and as already noted, the base unit may adopt a range of different forms. For example, whereas in the example represented in FIGS. 1A to 1C the base unit comprises a single receiving zone in the form of a tubular opening, in other examples a base unit may comprise multiple receiving zones for simultaneously treating a corresponding plurality of inhaler components. Furthermore, the receiving zones may comprise configurations other than a tubular recess.

Figure 12:
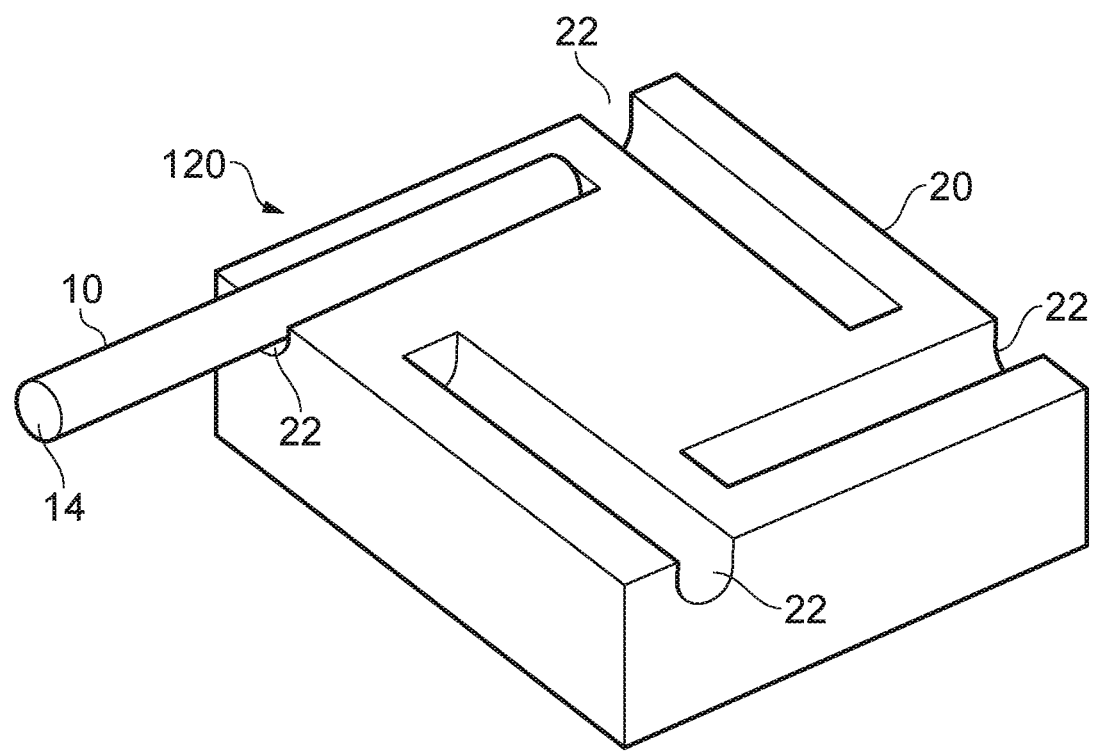
FIG. 12 represents in highly schematic perspective view a vapor provision system in accordance with certain other embodiments of the disclosure.

In this regard, FIG. 12 schematic represents a base unit 120 having a different design to the base unit schematically represented in FIGS. 1A to 1C. In this example the base unit 120 comprises four receiving zones 22 generally in the form of half-tube recesses in which an inhaler component (one example inhaler component 10 is shown in FIG. 12) may be laid. When an inhaler component is received in one of the receiving zones 22 its thermal store may be heated inductively in accordance with the principles described above. In this regard it will be appreciated the configuration of the induction coil will be different to that schematically represented in FIGS. 1A to 1C in that it will not completely surround the inhaler component, but will, in effect, be adjacent one side of the inhaler component. In this regard the induction coil may be a flat or curved coil. More generally the design and configuration of the induction coil may be chosen having regard to the well-established principles for inductive heating. For some geometries there may be a preferred orientation of the inhaler component with respect to the induction coil, and in this case the inhaler component may be marked to indicate the orientation to use (e.g. such that a decal on the inhaler component faces upwards or lined with a mark on the base unit). The base unit 120 represented in FIG. 12 may be provided with functionality of the kind discussed above for the base unit 20 represented in FIGS. 1A to 1C, albeit providing this functionality for a plurality of different receiving zones. Thus, the base unit 120 having a plurality of receiving zones may comprise a corresponding plurality of induction coils and activation sensors.

Thus, there has been described a vapor provision system comprising: an inhaler component and a base unit, wherein the inhaler component comprises a thermal store and a vapor precursor material; and the base unit comprises: a receiving zone for receiving the inhaler component; and a source of energy for heating the thermal store in the inhaler component when the inhaler component is located in the receiving zone such that heat is conducted from the heated thermal store to the vapor precursor material to vaporize at least a portion of the vapor precursor material to form a vapor for inhalation by a user when the inhaler component is removed from the receiving zone.

There has also been described a base unit for use in vapor provision system comprising the base unit and an inhaler component, wherein the base unit comprises a receiving zone for receiving the inhaler component and a source of energy for heating a thermal store in the inhaler component when the inhaler component is located in the receiving zone such that heat from the heated thermal store may be used to vaporize a portion of vapor precursor material to form a vapor for inhalation by a user when the inhaler component is removed from the receiving zone.

There has also been described an inhaler component for use in a vapor provision system comprising the inhaler component and a base unit, wherein the inhaler component comprises a thermal store arranged to be heated by a source of energy in the base unit when the inhaler component is received in a receiving zone of the base unit, such that heat from the heated thermal store may be used to vaporize a portion of vapor precursor material to form a vapor for inhalation by a user when the inhaler component is removed from the receiving zone.

The example embodiments described above have focused on approaches in which the base unit is configured to heat the thermal store in the inhaler component by electromagnetic induction. However, other techniques for transferring energy from the base unit to the thermal store can be used. For example, in some implementations the base unit may in effect comprise a hotplate/heater and the thermal store in the inhaler component may be arranged so that it is positioned in contact with/in proximity to the hotplate/heater when the inhaler component is placed in the receiving zone of the base unit so the thermal store is heated by thermal conduction. Other example approaches could involve optical heating of the thermal store when the inhaler component is placed in the base unit.

Furthermore, while some particular thermal store and vapor precursor material configurations have been described by way of example, it will be appreciated other configurations may be used. For example, rather than provide a thermal store in the form of a metallic sheet, the thermal store may have a block or rod shape, and may be solid or porous (e.g. comprising a metallic mesh, foam fibers or array of metallic particles). Furthermore, the thermal store need not be metallic, for example it may comprise an electrically conductive ceramic or a non-electrically conductive material in implementations which do not use inductive heating. Similarly, the vapor precursor material may adopt various form of liquid, solid, gel, paste or foam.

It will also be appreciated the base unit may for some implementations be provided with additional functionality. For example, in some cases the base unit may incorporate a means for measuring the temperature of the thermal store, for example based on detecting infrared radiation with a thermopile from the thermal store or using a thermocouple, or other temperature sensor. In this case the base unit may be configured to drive the transfer of energy to the thermal store of the inhaler component until an appropriate temperature is reached. In some implementations the inhaler components may be provided with an identifier, for example in the form of an RFID tag, which the base unit is configured to read. In such cases, the base unit may, for example, be configured to work only with certain inhaler components (e.g. inhaler components from a given supplier), or may be configured to operate differently for different types of inhaler components, example to heat differently depending on the identity of the inhaler component, for example to take account of different characteristics of vapor precursor materials or thermal store that may be used in different inhaler components.

Furthermore, in some examples the base unit may be configured to detect a characteristic of the inhaler component, e.g., a size or surface color or an electromagnetic characteristic of the susceptor, as it is inserted into the base unit, and to provide different amounts of energy to the thermal store based on this detection. For example, an inhaler component based on a liquid vapor precursor material may require less heat than an inhaler component based on a solid vapor precursor material so that an inhaler component based on a solid vapor precursor material has a larger thermal store. The base unit may be configured to detect the size of the thermal store (e.g. using conventional metal-detection techniques) and provide an appropriate amount of energy using the induction heating coil).

Figure 13A:
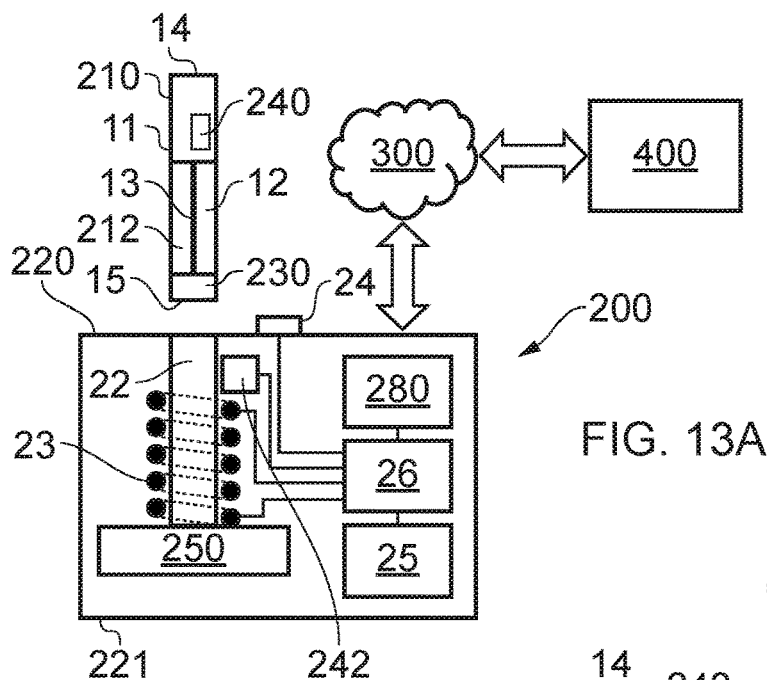
FIGS. 13A to 13C represent in highly schematic cross-section a vapor provision system in accordance with certain embodiments of the disclosure at different stages of use.
Figure 13B:
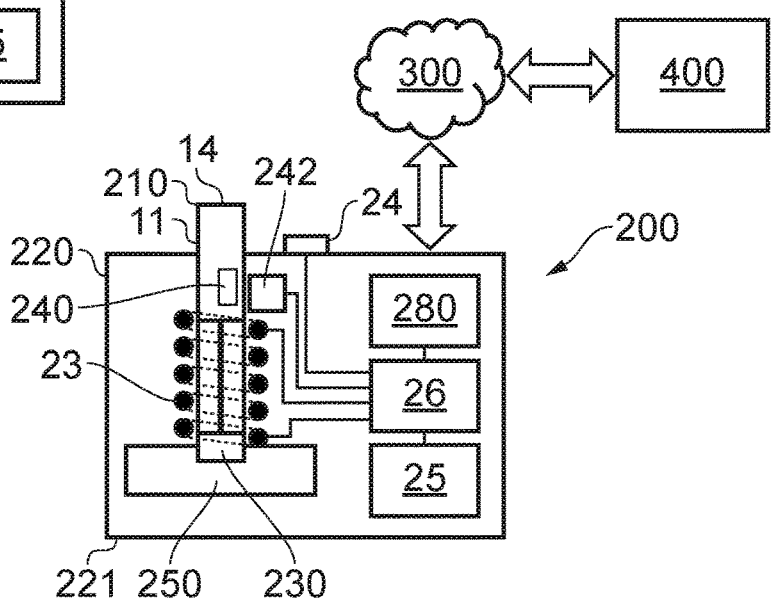
Figure 13C:
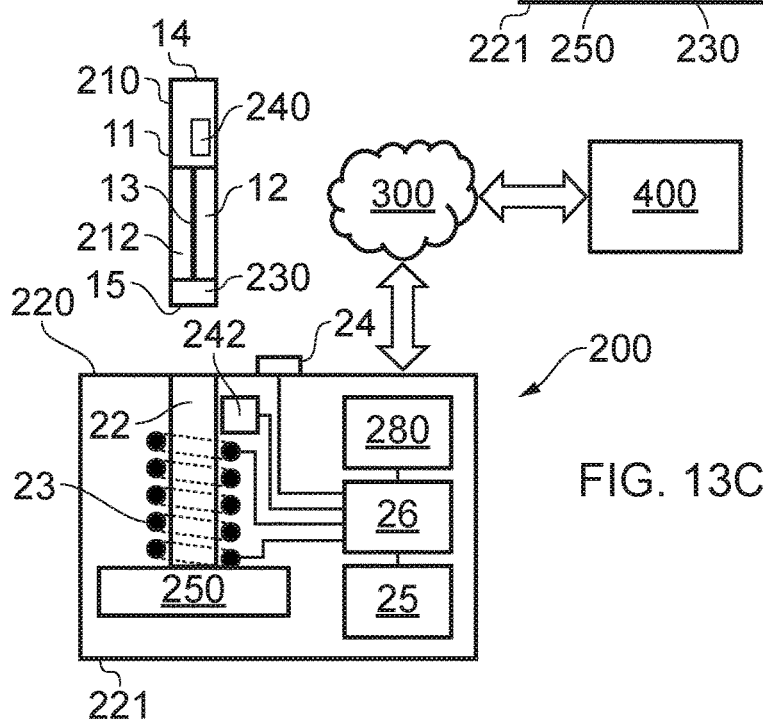

FIGS. 13A to 13C represent in highly schematic cross-section a vapor provision system 200 in accordance with certain other embodiments of the disclosure at different stages of use. Elements of the vapor provision system 200 represented in FIGS. 13A to 13C which are functionally and/or structurally similar to, and will be understood from, corresponding elements of the vapor provision system 2 represented in FIGS. 1A to 1C are identified with corresponding reference numerals and are not discussed again in detail in the interests of brevity since further details of these elements are as already set out above. The vapor provision system 200 of FIGS. 13A to 13C differs from the vapor provision system 2 of FIGS. 1A to 1C by virtue of the base unit providing additional functionality in relation to establishing records of the provision of a consumable used by the inhaler component to generate vapor for user inhalation (e.g. energy vapor and/or precursor material) in association with an identifier associated with the inhaler component (e.g. an identifier for the inhaler component itself or a user associated with the inhaler component). The records of the provision of the consumable to the inhaler component may be used, for example, for user billing and/or market research purposes.

Thus the system 200 represented in FIGS. 13A to 13C again comprises an inhaler component 210 and a base unit 220.

The inhaler component 210 represented in FIGS. 13A to 13C is in this example in many respects similar to, and will be understood from, the inhaler component 10 represented in FIGS. 1A to 1C and discussed above. However, the inhaler component 210 represented in FIGS. 13A to 13C is different in comprising an identifier for the inhaler component, which in this example comprises a radio frequency identity (RFID) tag 240, and a wick element 230 at the inlet end 15 of the inhaler component 210 which is contact with absorbent wadding material 212 for holding the vapor precursor material 12 in the vicinity of the thermal store/ susceptor 13. In this example the absorbent wadding material 212 comprises organic cotton, but as noted above in relation to the inhaler component 10 in FIGS. 1A to 1C, in other examples the wadding material may comprise other absorbent materials, for example fiberglass, steel wool, paper, ceramic fibers, tobacco material and so forth.

The RFID tag 240 may be based on conventional RFID tagging techniques. The RFID tag may comprise an identifier for the inhaler component incorporated in the inhaler component during manufacture, or during subsequent programming (for example when a user purchases the inhaler component, the RFID tag may be programmed with an identifier associated with the user).

The wick element 230 at the inlet end 15 of the inhaler component is arranged so that when the inlet end 15 of the inhaler component in 10 is dipped into a reservoir of liquid vapor precursor material (which in this example is provided by the base unit), the vapor precursor material is drawn through the wick element 230 towards the absorbent wadding material 212 so that the absorbent wadding material 212 becomes infiltrated with liquid vapor precursor material drawn from the reservoir of liquid vapor precursor material so as to prepare the inhaler component for vapor generation, e.g. by inductive heating, as discussed above.

The base unit 220 represented in FIGS. 13A to 13C is in this example in many respects similar to, and will be understood from, the base unit 20 represented in FIGS. 1A to 1C and discussed above. However, the base unit 220 represented in FIGS. 13A to 13C is different in comprising an identifier reader 240 for reading the identifier from the inhaler component 210 when the inhaler component is received in the receiving zone 22, a liquid supply chamber 250 for holding liquid vapor precursor material for provision to the inhaler component, and a communications interface 280 coupled to the control circuitry 26 for supporting communications between the base unit and a remote server 400 via the internet 300.

The identifier reader 242 in this example comprises a conventional RFID tag reader that is located in the base unit 210 so as to read the identifier for the inhaler component 210 stored in its RFID tag 240 when the inhaler component is placed in the receiving zone 22. In this regard the identifier reader 240 may be configured to operate in accordance with conventional techniques, and may, for example be configured to read the identifier from the inhaler component in response to detecting the inhaler component is first placed in the receiving zone. Thus, the identifier reader 242 in the base unit and the RFID tag 240 in the inhaler component operate together to allow the base unit to establish an identifier for the inhaler component when the inhaler component is received in the receiving zone 22 of the base unit, or in other example implementations, otherwise coupled to the base unit. It will be appreciated that in other examples other approaches may be provided to allow the base unit to establish an identifier for the inhaler component. For example, the inhaler component may have a barcode, QR code, or other code marked on its surface which is optically detected by the identifier reader 242 in the base unit to establish the identifier for the inhaler component. More generally, any known scheme by which an identifier may be incorporated into the inhaler component and detected/read by the base unit may be adopted in accordance with different embodiment of the disclosure. That is to say, what is significant for certain embodiments of the disclosure is that the base unit is able to establish an identifier for the inhaler component, but the specific manner in which the base unit establishes this identifier is not of primary significance to the principles described herein.

The liquid supply chamber 250 is arranged at the end of the receiving zone 22 such that when the liquid supply chamber 250 contains liquid vapor precursor material, and an inhaler component is placed in the receiving zone 22, the absorbent wick 230 at the end of the inhaler component 210 contacts liquid in the liquid supply chamber and the liquid is drawn into the inhaler component 210 to infiltrate the absorbent wadding 212 adjacent the thermal store/susceptor 13. The liquid supply chamber 250 thus provides a mechanism for providing the inhaler component with vapor precursor material. In this example the provision of the liquid vapor precursor material to the inhaler component is based on simple absorption from a reservoir. That is to say, the absorbent wick 230 of the inhaler component is in effect simply dipped into a reservoir of liquid to absorb the liquid. The liquid supply chamber 250 might be a relatively large chamber containing enough liquid to supply many inhaler components, and may be automatically topped up by the base unit from a source of liquid to maintain an appropriate level. Alternatively, the liquid supply chamber to 50 might be relatively small, for example containing only enough liquid for one inhaler component, and may be filled with liquid by the base unit from a supply of liquid on a per-use basis. In some examples an inhaler component might not comprise a separate absorbent wick 230, and a portion of the absorbent wadding material 212 for holding liquid vapor precursor material in the vicinity of the thermal store may itself be dipped directly into the liquid reservoir to absorb the liquid vapor precursor material provided by the base unit. Still other approaches may be taken in other implementations. For example, the base unit may be provided with a pump arranged to drive an amount of liquid vapor precursor material into the relevant part of the inhaler component. More generally, any scheme by which the inhaler component is provided with vapor precursor material may be adopted in accordance with different embodiment of the disclosure. That is to say, what is significant is that the base unit is able to provide the inhaler component with an amount of vapor precursor material, and the specific manner in which the base unit is configured to do this is not of primary significance to the principles described herein.

As noted above, the communications interface 280 allows the base unit to communicate with a remote server 400, in this example via the Internet 300. The specific nature of the communications interface 280, for example in terms of the link architecture and communications protocols used, is not of primary significance to the principles described herein, and the communications interface may operate in accordance with conventional techniques, for example based on wired or wireless connections to the Internet, and may connect to the Internet directly or via an intermediate network, for example a mobile telecommunications network. In some examples the base unit may connect to the remote server 400 directly, for example over a private network/communication route, rather than via the Internet.

Having discussed the overall structure and configuration of the vapor provision system 200 represented in FIGS. 13A, 13B and 13C, and in particular in respect of how it differs from the vapor provision system 20 represented in FIGS. 1A, 1B and 1C, an example use of the system 200 will now be described. In this regard it is assumed FIG. 13A schematically represents a situation in which an un-used inhaler component is about to be used for the first time after having been purchased by a user. In accordance with this example, it is assumed the inhaler component is initially supplied in a dry state, i.e. without any liquid vapor precursor material. It is further assumed for this example the inhaler component RFID tag 240 comprises an indication of an identifier for the inhaler component which is encoded into the RFID tag during manufacture. For the sake of providing an example usage scenario, it is assumed here that when a user purchases the inhaler component, its identifier is listed against an account for the user, details of which may be stored in the server 400. That is to say, a record is retained in the server 400 to indicate which users are associated with which inhaler component identifiers. This is so that subsequent use of an inhaler component with a base unit in accordance with the principles described herein may be matched to a particular user, for example for billing and/or market research purposes. The record may be received and retained in the server in accordance with conventional techniques, for example making use of a communications link between a point of sale terminal and the server.

Thus, in FIG. 13A the inhaler component 210 is shown on approach to the receiving zone 22 of the base unit 220. At this stage the susceptor/heat store 13 in the un-used inhaler component 210 is cold (i.e. at ambient temperature) and the absorbent wadding 212 surrounding the susceptor/thermal store 13 does not contain any liquid vapor precursor material.

FIG. 13B shows the inhaler component 210 when it is received in the receiving zone 22 of the base unit 220. As discussed above, in this arrangement the base unit is configured to detect the identifier for the inhaler component by reading the RFID tag 240 in the inhaler component 210 using the identifier reader 242 and also the inhaler component's absorbent wick 230 extends into the base unit's liquid supply chamber 250 so that liquid vapor precursor material stored in the liquid supply chamber 250 is absorbed into the inhaler component and drawn into the reservoir wadding 212 adjacent the thermal store 13. In effect, the base unit thus provides the inhaler component with an amount of liquid vapor precursor material for subsequent use in generating vapor for user inhalation. In this example the provision of the vapor precursor material consumable to the inhaler component is passive, in that it relies on simple absorption. A user may thus be made aware that they should leave the inhaler component coupled to the base unit for at least a minimum amount of time to allow sufficient liquid to be drawn into the inhaler component. In other examples in which the base unit actively drives the provision of vapor precursor material to the inhaler component, for example through a pump system, the base unit may be configured to detect when the inhaler component is initially coupled to the base unit (i.e. in this example placed in the receiving zone), and trigger the supply of the vapor precursor material accordingly. When the appropriate amount of vapor precursor material has been provided to the inhaler component, the base unit may indicate this, for example by changing the status of an indicator light so the user can recognize when provision of the liquid vapor precursor material is complete.

Once the vapor precursor material has been provided to the inhaler component (e.g. after a sufficient amount of time for the liquid to be drawn from the liquid refill chamber to the inhaler component), the inhaler component is ready to be withdrawn/uncoupled from the base unit and to generate vapor for user inhalation. This may be performed in accordance with the principles described above, for example with the inductive coil 23 being used to heat the susceptor/thermal store 13 when it is detected the inhaler component 210 is to be removed from the receiving zone 22 for use based on signaling from the activation centre 24.

FIG. 13C schematically represents the inhaler component 210 having been removed from the base unit 220 after the base unit has provided the inhaler component with the, in this example, two different types of consumable, namely an amount of vapor precursor material and an amount of energy, for use in generating vapor for user inhalation. At this stage the inhaler component 210 is ready for use in the manner described above (i.e. a user may inhale on the mouthpiece end 14 to draw air in through the inlet 15 and along the airflow path defined by the housing 11 as the heat in the thermal store vaporizes a portion of the vapor precursor material for user inhalation).

Having taken a puff on the inhaler component and inhaled a portion of the vapor, the user may in some cases continue to hold the inhaler component ready for a second puff in the event there is enough vapor precursor material and thermal energy remaining to provide for another inhalation event (puff). In other cases the user may need to return the inhaler component to the base unit to be recharged with energy and/or vapor precursor material for another puff.

Thus, in terms of the manner in which vapor is generated for user inhalation, the vapor provision system 200 represented in FIGS. 13A to 13C may operate broadly in the same way as the vapor provision system two represented in FIGS. 1A to 1C, albeit in the example of FIGS. 13A to 13C, the base unit 220 is configured to provide the inhaler component 210 with an amount of vapor precursor material in addition to an amount of energy for use in generating vapor for user inhalation.

Thus, during the process represented in 13A to 13C, the base unit 220 is configured to establish an identifier for an inhaler component 210 that is coupled to the base unit, and to provide the inhaler component with an amount of consumable (in this case both vapor precursor material and energy, although in other examples only one or other of these may be provided). The base unit in accordance with certain example implementations of the disclosure is further configured to maintain a record of the fact the energy and/or vapor precursor material has been provided to the inhaler component in association with the identifier for the inhaler component. This record may be maintained in the base unit and/or transferred to the remote server. The record may be used for a number of different purposes, for example user billing, market research, and/or restricting the number of times a given inhaler component may be reused.

Figure 14:
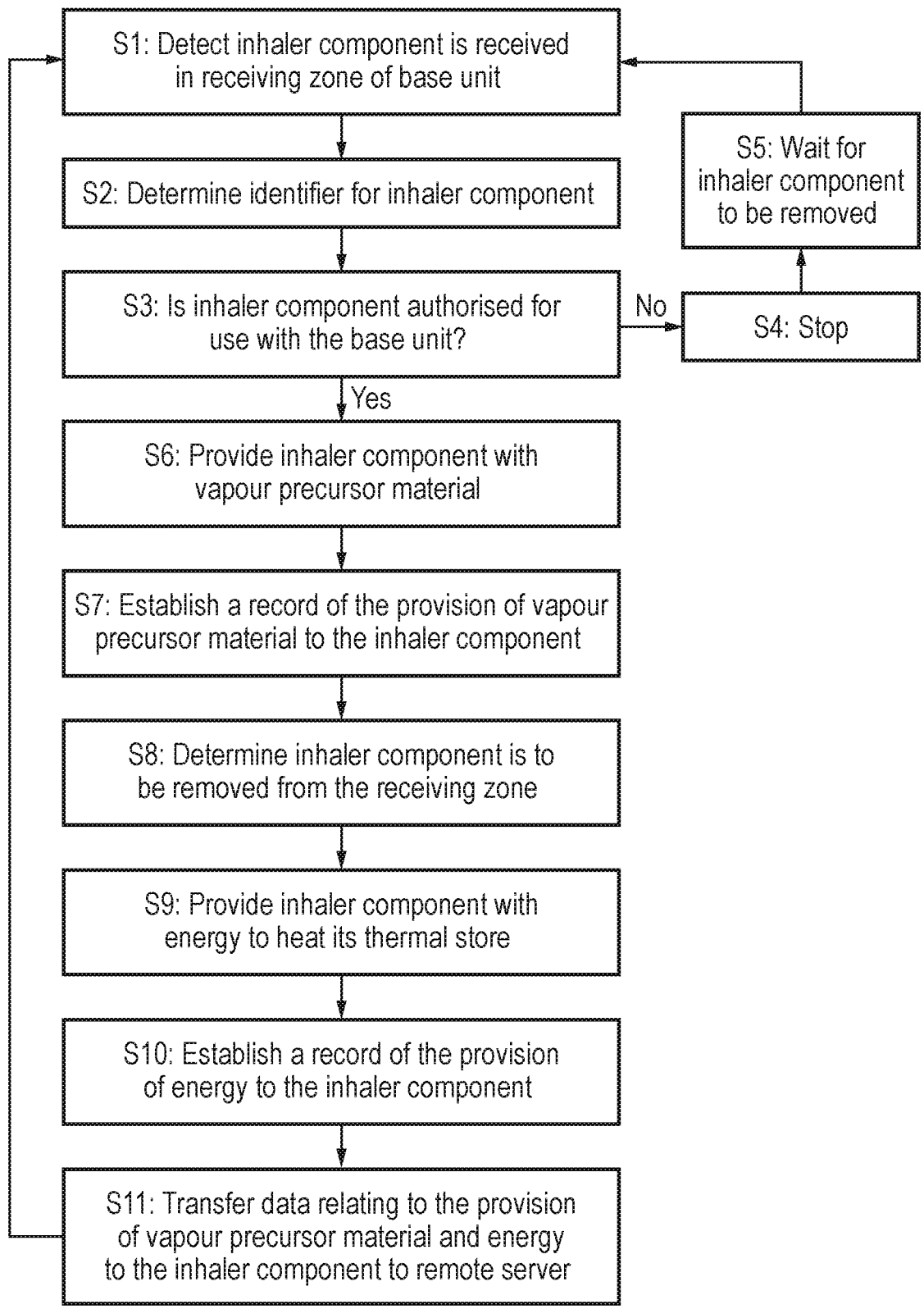
FIG. 14 is a flow diagram schematically representing a method of operation for the vapor provision system represented in FIGS. 13A to 13C.

FIG. 14 is a flow diagram schematically representing steps associated with certain aspects of the operation of the base unit 220 in relation to establishing a record of the provision of energy/vapor precursor material (or more generally a consumables used for vapor generation) to the inhaler component 210.

Processing starts in 51 in which the base unit detects the inhaler component is received in the receiving zone of the base unit (or otherwise coupled to the base unit depending on the implementation at hand). There are various different ways the base unit can detect when the inhaler component placed in the receiving zone, for example a mechanical switch may be activated by the presence of the inhaler component, or an optical sensor may detect the presence of the inhaler component. In this example, in which the base unit comprises an identifier reader 242 for the RFID tag 240 in the inhaler component, it is assumed the identifier reader 242 readily scans for the presence of an RFID tag in accordance with usual techniques for RFID detection, and when the identifier reader is able to detect and read an RFID tag, the base unit determines an inhaler component is present in the receiving zone.

In S2, the base unit determines the identifier for the inhaler component. In this example the identifier is read from the RFID tag 240 in accordance with conventional RFID techniques. However, and as noted elsewhere herein, there are various other ways in which the base unit may establish the identifier associated with the inhaler component in different implementations, for example in some cases an approach based on using a barcode reader or manual user-input might be used.

In S3, the base unit in this example determines whether or not the inhaler component is authorized for use with the base unit. This may, for example, be based on the identifier determined in S2. For example, the base unit may be configured to only operate with inhaler components provided by a given manufacturer, with inhaler components from the manufacturer being configured to incorporate a unique code into their identifiers.

If it is determined in S3 that the inhaler component currently coupled to the base unit is not authorized for use with the base unit, processing follows the branch marked "No" to S4 in which the processing stops until the non-authorized inhaler component is removed from the base unit (as schematically indicated in S5), and another inhaler component is detected in the receiving zone (as schematically indicated by the return to 51 from S5 in FIG. 14).

If it is determined in S3 that the inhaler component currently coupled to the base unit is authorized for use with the base unit, processing follows the branch marked "Yes" to S6.

In S6 the base unit provides the inhaler component with an amount of vapor precursor material. As noted above, for the example system represented in FIGS. 13A to 13C, this may, in effect, happen automatically by virtue of the inhaler component absorbing liquid from a chamber in the base unit. As also noted above, the base unit may provide the inhaler component with vapor because material in a more positive manner, for example by pumping liquid into the inhaler component or an intermediate chamber. In some examples S6 may include a determination of the amount of vapor precursor material provided to the inhaler component, whereas in other examples a predetermined fixed amount of vapor precursor material may be provided for each use, or the amount provided may not be determined. Where the amount of vapor precursor material provided to the inhaler component is determined, there are various ways in which this can be done. For example, by a metering pump system, or by determining how long the absorbent part of the inhaler component is immersed in the liquid (with an assumption on the rate of absorption), or by observing a reduction in the volume of liquid in the liquid supply chamber (for example based on weight or liquid level measurements).

In S7 the base unit establishes a record that the inhaler component associated with the identifier detected in S2 has been provided with an amount of vapor precursor material in S6, and optionally, where measured, an indication of the amount of the vapor precursor material provided to the inhaler component in S6.

In S8 the base unit determines the inhaler component is to be removed from the receiving zone. This may be performed in accordance with any of the approaches described above.

In S9, on detecting the inhaler component is being, or about to be, removed from the receiving zone (i.e. decoupled from the base unit), the base unit provides the inhaler component with energy to heat its thermal store. In this example implementation this may be performed using the induction heating coil to transfer electromagnetic energy to the susceptor in the inhaler component in accordance with the approaches described herein. In some examples S9 may include a determination of the amount of energy provided to the inhaler component, whereas in other examples a predetermined fixed amount of energy may be provided for each use, or the amount provided may not be determined. Where the amount of energy provided to the inhaler component is determined, there are various ways in which this can be done, for example, measuring the amount and duration of current supplied to the induction coils.

In S10 the base unit is configured to establish a record that the inhaler component associated with the identifier detected in S2 has been provided with an amount of energy in S9, and optionally, where measured, an indication of the amount of the energy provided to the inhaler component in S9. In practice, in an implementation in which the base unit is configured to provide the inhaler component with both vapor precursor material and energy, a single record may be created to capture this. That is to say, the record established at S10 and the record established at S7 may comprise the same record with indications relating to the provision of the respective consumables.

In S11, the base unit transfers data relating to the provision of the vapor precursor material and the energy to the inhaler component to the remote server 400 in conjunction with the relevant identifier.

Thus, at the end of the processing represented in FIG. 14, the base unit has provided the inhaler component with energy and vapor precursor material to allow the inhaler component to be used for vapor generation for user inhalation. Furthermore, the base unit has established a record that this has happened in association with the inhaler component identifier, and transferred an indication of this to the remote server.

There are many different ways in which the data transferred to the server may be of use in a system of the kind described herein. For example in some implementations this information may be used for billing purposes. For example individual users may have accounts logged at the server, and whenever a base unit transfers data to the server indicating an inhaler component with an identifier associated with the user has received vapor precursor material and/or energy from the base unit, the relevant user's account may be debited accordingly. In addition, or instead, the data transferred back to the server may be used for market research purposes, for example to determine how often a given inhaler component is used. It will be appreciated this approach is based on a centralized server which may support a plurality of base units at different locations. In other cases the base unit may be stand-alone and retain a local copy of the relevant records. Thus, in one use scenario, a base unit in a bar may be used throughout an evening by a user to repeatedly provide their inhaler component with energy vapor and/or precursor material, and at the end of the evening the user may be presented with an appropriate bill based on their usage of the base unit throughout the evening.

It will be appreciated that many modifications and adaptions may be made to the vapor provision systems described above in accordance various other embodiments of the disclosure.

For example, in the vapor provision system 200 represented in FIGS. 13A to 13C, the identifier for the inhaler component is specific to the inhaler component itself. That is to say, the identifier identifies the inhaler component.

However, in another example the identifier for the inhaler component may not be specific to the inhaler component, but may instead be specific to a user associated with the inhaler component. That is to say, the identifier may identify the user associated with the inhaler component rather than the inhaler component itself. In some such examples, instead of the base unit establishing an identifier for the inhaler component by detecting a characteristic of the inhaler component (e.g. by reading/detecting an RFID tag or surface markings, such as barcode, QR code or other printed code or other data exchange), the base unit may instead establish an identifier for an inhaler component coupled to the base unit from user input. For example, the base unit may be provided with a numeric input panel or swipe card reader and users may each have their own personal identification number or swipe card allocated to them for use with the vapor provision system. When a user wishes to replenish a consumable in an inhaler component (i.e. receive an amount of vapor precursor material and/or power from the base unit), they may enter their PIN code or swipe their swipe card when, or just before, the inhaler component is coupled to the base unit (i.e. placed in a receiving zone of the base unit or connected to a wired connector of the base unit). The user's PIN code or swipe card data may thus become the identifier for the inhaler component and may be used as the basis for the record established to indicate the inhaler component has received the consumable from the base unit. In that sense, it will be appreciated in some example implementations, records indicating which inhaler components have received an amount of consumable from the base unit may in effect indicate which users have received the consumable from the base unit.

Typically it may be expected the data which is most of interest is the users that have received the consumable, for example so they can be billed accordingly or to help obtain usage profiles for specific users for market research purposes, and this approach can facilitate that. Nonetheless, it will be appreciated approaches in which the identifier is specific to the electronic cigarette can also be used to match usage to specific users by establishing a correspondence between identifiers specific to individual inhaler components with users, for example specific inhaler components may be registered for use by specific users in a database stored in the base unit and/or a remote server so that specific inhaler components can be mapped to specific users.

However, it will also be appreciated that in some implementations there may be no desire to associate specific users with individual inhaler components, in which case the identifier may simply identify the inhaler component itself with no need to match this to a particular user. For example, in one usage scenario, an inhaler component of the kind represented in FIGS. 13A to 13C may be provided to a user on the basis it may be used with the base unit a predefined number of times, for example 10 times, after which it becomes unusable. A user may therefore purchase one inhaler component, and each time it is used in the base unit, the base unit establishes a record of that use for that inhaler component, and when the predefined number of allowed uses has been reached, the base unit may be configured to stop providing the inhaler component with the relevant consumable (e.g. power or vapor precursor material). In such a scenario the inhaler component may be "locked" to the particular base unit with which it is first used so that the number of previous uses only need storing in the base unit, and in other cases the inhaler component may be allowed for use with a plurality of different base units, for example at different geographical locations, in which case a record of the number of previous uses may be stored in a central server to which each base unit is connected.

Furthermore, it will be appreciated that whereas the above-described examples have focused on a specific implementation of what might be termed a minimalist inhaler component comprising a thermal store and a source of vapor precursor material, aspects of the embodiments described above relating to the provision of a consumable to an inhaler component and the recording of data relating to the provision of a consumable to an inhaler component may equally be applied for more conventional electronic cigarettes. For example, the approach described above may also be implemented for an inhaler component that in effect comprises a fully functional electronic cigarette comprising a battery/cell, control electronics, vaporizer and vapor precursor material. Such a device may still benefit from being coupled to a base unit to receive energy (e.g. for recharging the battery/cell) or vapor precursor material (e.g. when the device is running out) from a base unit. In some implementations a base unit may be configured to provide electrical energy to charge the rechargeable battery of an inhaler component through a conventional wired connector, for example such as a USB connector. In that sense, coupling and decoupling the inhaler component to/from the base unit may correspond with connecting/disconnecting the wired connection from the base unit to the inhaler component. The base unit may be configured to establish an identifier for an inhaler component coupled to the base unit through a wired connection via data exchange over the wired connection, or other means such as discussed above (e.g. based on an RFID tag or other coding on the inhaler component itself, or user input, such a user PIN code or swipe card data).

Instead of a wired connection, electrical energy for recharging a rechargeable cell in an inhaler component may also be provided by a base unit in a wireless manner, for example using inductive charging techniques, when the inhaler component is placed in a receiving zone of the base unit.

In some example implementation the base unit may be not be configured to provide the inhaler component with both energy and vapor precursor material, but may only provide one or other. Furthermore, the base unit may be configured to provide vapor precursor material in forms other than liquid, for example an amount of solid vapor precursor material may be provided to the inhaler component, for example by mechanically introducing the solid vapor precursor material to the inhaler component at an appropriate location. In other examples a gel, foam or paste vapor precursor material may be provided to the inhaler component, for example under pressure to in effect squeeze the vapor precursor material into the relevant part of the inhaler component. More generally, it will be appreciated the specific nature of the vapor precursor material and the manner in which it is provided to the inhaler component is not of primary significance to the principles described herein regarding the establishment of a record of the provision of the vapor precursor material, or other consumable, to the inhaler component.

In some examples, the inhaler component may be configured to maintain a record of usage, for example by recording times and durations of use by a user, in a memory, and this data may be transferred to the base unit when the inhaler component is coupled to the base unit to receive an amount of energy vapor and/or precursor material. This usage data may then be communicated back to a remote server in a manner similar to that described above for the record indicating the provision of the consumable to the inhaler component. This data may then be used for market research purposes. For example, in one implementation, a base unit may be configured to provide energy to charge a battery of an electronic cigarette for free on the understanding the usage data is provided to the base unit for transfer to the server for market research purposes. The usage data may be recorded/transmitted by the base unit anonymously or in association with the identifier depending on the application at hand.

In some examples a base unit may be configured to provide different types of a consumable, for example different flavors of vapor precursor material, e.g. by providing multiple receiving zones in which an inhaler component may be coupled to the base unit to receive vapor precursor material, with each receiving zone providing vapor precursor material with a different flavor. A user may select a desired flavor by coupling their inhaler component to the base unit in a corresponding receiving zone. Alternatively the base unit may be configured to supply different vapor precursor material flavors in a single receiving zone and user input may be used to determine which flavor to provide, e.g. through a menu of buttons. The record of the provision of the consumable to the inhaler component established by the base unit may include an indication of the flavor, for example for market research or pricing purposes.

It will be appreciated various features discussed above in relation to using an inhaler component with a base unit configured to provide aerosol precursor material and/or power and/or collect use data may be provided in some examples independently of other features. For example, in some cases an inhaler component of the kind discussed above in relation to FIGS. 13A to 13C may be used with a base unit that does not provide power/energy to or track usage of the inhaler component. For example, the base unit may, in effect, simply comprise be a housing containing vapor precursor material, e.g. in the form of a liquid, paste, gel or solid, that may be transferred to the inhaler component for vaporization. The inhaler component may, for example, comprise its own vaporizer/heater, or the vapor precursor material may be sufficiently volatile as to be inhalable without a vaporizer (it may be warmed/heated in the base unit before transfer to the inhaler component to facilitate this). It will be appreciated this kind of simple (e.g. non-powered) base unit for providing vapor precursor material to an inhaler component, e.g. by simply dipping the inhaler component in the vapor precursor material, may comprise a plurality of vapor precursor materials, e.g. with different flavors and/or nicotine strengths, or other characteristics.

Thus, there has been described an electronic vapor provision system comprising: an inhaler component for generating a vapor from a vapor precursor material; and a base unit comprising a receiving zone for receiving the inhaler component; wherein the base unit is configured to establish an inhaler component identifier associated with the inhaler component when it is received in the receiving zone and to provide the inhaler component with an amount of energy and/or an amount of aerosol precursor material so the inhaler component is able to form a vapor for inhalation by a user when the inhaler component is removed from the receiving zone; and wherein the base unit is further configured to establish a record indicating the inhaler component associated with the inhaler component identifier has been provided with the amount of energy and/or the amount of aerosol precursor material.

There has also been described an inhaler component for use in the electronic vapor provision system. For example, an inhaler component for generating vapor from a vapor precursor material for an electronic vapor provision system comprising the inhaler component and a base unit, wherein the base unit and the inhaler component may be selectively coupled and uncoupled; wherein the inhaler component is associated with an identifier that is provided to the base unit, and wherein the inhaler component is configured to receive an amount of consumable from the base unit when the inhaler component is coupled to the base unit and to generate vapor for user inhalation when the inhaler component is uncoupled from the base unit.

There has also been described a base unit for use in the electronic vapor provision system. For example, a base unit for an electronic vapor provision system comprising the base unit and an inhaler component for generating vapor from a vapor precursor material, wherein the base unit and the inhaler component may be selectively coupled and uncoupled; wherein the base unit is configured to establish an identifier for an inhaler component coupled to the base unit and, when the inhaler component is coupled to the base unit, to provide the inhaler component with an amount of consumable for use by the inhaler component for generating vapor for user inhalation when the inhaler component is uncoupled from the base unit; wherein the base unit is further configured to establish a record of the identifier for the inhaler component in association with an indication the consumable has been provided to the inhaler component.

There has also been described a server for use with the electronic vapor provision system. For example, a server configured to connect to a remote base unit of an electronic vapor provision system comprising the base unit and an inhaler component, wherein the base unit is configured to establish an identifier for the inhaler component and to provide the inhaler component with a consumable for use by the inhaler component for generating vapor for user inhalation when the inhaler component is uncoupled from the base unit, and wherein the server is configured to receive from the base unit an indication of a record of the identifier for the inhaler component in association with an indication the consumable has been provided by the base unit to the inhaler component.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An electronic vapor provision system comprising:
   an inhaler component for generating vapor from a vapor precursor material, and a base unit to which the inhaler component may be selectively coupled and uncoupled;

wherein the base unit is configured to establish an identifier for the inhaler component and, when the inhaler component is coupled to the base unit, to provide the inhaler component with an amount of consumable for use by the inhaler component for generating vapor for user inhalation when the inhaler component is uncoupled from the base unit;

wherein the base unit is further configured to establish a record of the identifier for the inhaler component in association with an indication the consumable has been provided to the inhaler component, and wherein the indication the consumable has been provided to the inhaler component comprises an indication of the amount of the consumable that has been provided to the inhaler component by the base unit.

2. The electronic vapor provision system of claim 1, wherein the consumable provided by the base unit to the inhaler component comprises energy for use in vaporizing vapor precursor material.

3. The electronic vapor provision system of claim 2, wherein the inhaler component comprises a rechargeable cell, and the energy comprises electrical energy for charging the rechargeable cell.

4. The electronic vapor provision system of claim 2, wherein the inhaler component comprises an electromagnetic susceptor, and the energy comprises electromagnetic energy for inductively heating the electromagnetic susceptor.

5. The electronic vapor provision system of claim 1, wherein the vapor precursor material comprises a liquid vapor precursor material and the inhaler component comprises an absorbent element for receiving the liquid vapor precursor material provided by the base unit.

6. The electronic vapor provision system of claim 1, wherein the base unit comprises a receiving zone for receiving the inhaler component, and the inhaler component is coupled to the base unit by placing the inhaler component in the receiving zone.

7. The electronic vapor provision system of claim 1, wherein the base unit comprises a wired connector and the inhaler component is coupled to the base unit by connecting the wired connector to the inhaler component.

8. The electronic vapor provision system of claim 1, wherein the inhaler component comprises an indication of the identifier and the base unit is configured to establish the identifier by detecting the indication of the identifier when the inhaler component is coupled to the base unit.

9. The electronic vapor provision system of claim 8, wherein the indication of the identifier is provided by at least one of a radio frequency identification chip or a machine readable marking on the inhaler component.

10. The electronic vapor provision system of claim 1, wherein the base unit comprises a user interface and is configured to establish the identifier for the inhaler component from user input received through the user interface.

11. The electronic vapor provision system of claim 1, wherein the identifier for the inhaler component identifies the inhaler component itself.

12. The electronic vapor provision system of claim 1, wherein the base unit is further configured to transmit to a remote server an indication of the record of the identifier for the inhaler component in association with the indication the consumable has been provided to the inhaler component.

13. The electronic vapor provision system of claim 1, wherein the inhaler component is configured to establish a record of usage data relating to use of the inhaler component, and to transfer the indication of the usage data to the base unit when the inhaler component is coupled to the base unit.

14. The electronic vapor provision system of claim 13, wherein the base unit is further configured to transmit to a remote server an indication of the record of usage data relating to use of the inhaler component in association with the indication of the identifier for the inhaler component.

15. The electronic vapor provision system of claim 1, wherein the consumable comprises vapor precursor material.

16. An inhaler component for generating vapor from a vapor precursor material for an electronic vapor provision system comprising the inhaler component and a base unit, wherein the base unit and the inhaler component may be selectively coupled and uncoupled; wherein the inhaler component is associated with an identifier that is provided to the base unit, wherein the inhaler component is configured to receive an amount of consumable from the base unit when the inhaler component is coupled to the base unit and to generate vapor for user inhalation when the inhaler component is uncoupled from the base unit, wherein the indication the consumable has been provided to the inhaler component comprises an indication of the amount of the consumable that has been provided to the inhaler component by the base unit.

17. An electronic vapor provision system comprising:
an inhaler component for generating vapor from a vapor precursor material, and
a base unit to which the inhaler component may be selectively coupled and uncoupled;
wherein the base unit is configured to establish an identifier for the inhaler component and, when the inhaler component is coupled to the base unit, to provide the inhaler component with an amount of consumable for use by the inhaler component for generating vapor for user inhalation when the inhaler component is uncoupled from the base unit;
wherein the base unit is further configured to establish a record of the identifier for the inhaler component in association with an indication the consumable has been provided to the inhaler component; and
wherein the identifier for the inhaler component identifies a user associated with the inhaler component.

18. An electronic vapor provision system comprising:
an inhaler component for generating vapor from a vapor precursor material, and
a base unit to which the inhaler component may be selectively coupled and uncoupled;
wherein the base unit is configured to establish an identifier for the inhaler component and, when the inhaler component is coupled to the base unit, to provide the inhaler component with an amount of consumable for use by the inhaler component for generating vapor for user inhalation when the inhaler component is uncoupled from the base unit;
wherein the base unit is further configured to establish a record of the identifier for the inhaler component in association with an indication the consumable has been provided to the inhaler component; and
wherein the base unit is further configured to establish from the identifier for the inhaler component whether the inhaler component is authorized for use with the base unit, and to provide the inhaler component with the consumable only if the determination is made that the inhaler component is authorized for use with the base unit.

19. An inhaler component for generating vapor from a vapor precursor material for an electronic vapor provision system comprising the inhaler component and a base unit, wherein the base unit and the inhaler component may be selectively coupled and uncoupled; wherein the inhaler component is associated with an identifier that is provided to the base unit, wherein the identifier for the inhaler component identifies a user associated with the inhaler component and wherein the inhaler component is configured to receive an amount of consumable from the base unit when the inhaler component is coupled to the base unit and to generate vapor for user inhalation when the inhaler component is uncoupled from the base unit.

20. An inhaler component for generating vapor from a vapor precursor material for an electronic vapor provision system comprising the inhaler component and a base unit, wherein the base unit and the inhaler component may be selectively coupled and uncoupled; wherein the inhaler component is associated with an identifier that is provided to the base unit, wherein the inhaler component is configured to receive an amount of consumable from the base unit when the inhaler component is coupled to the base unit and to generate vapor for user inhalation when the inhaler component is uncoupled from the base unit and; wherein the base unit is further configured to establish from the identifier for the inhaler component whether the inhaler component is authorized for use with the base unit, and to provide the inhaler component with the consumable only if the determination is made that the inhaler component is authorized for use with the base unit.

\* \* \* \* \*